US006620588B1

(12) United States Patent
Bushman et al.

(10) Patent No.: US 6,620,588 B1
(45) Date of Patent: Sep. 16, 2003

(54) METHOD OF IDENTIFYING INHIBITORS OF TOPOISOMERASE DNA RELIGATION

(75) Inventors: Frederic Bushman, Encinitas, CA (US); Young Hwang, San Diego, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 09/583,342

(22) Filed: May 31, 2000

(51) Int. Cl.[7] .......................... G01N 33/53; C12N 9/90; C07H 21/04; C12Q 1/68; C12P 19/34
(52) U.S. Cl. .......................... 435/7.1; 435/6; 435/91.1; 435/233; 536/22.1; 536/24.2; 536/24.3
(58) Field of Search .................. 435/7.1, 233; 536/22.1; 436/501

(56) References Cited

U.S. PATENT DOCUMENTS 5,998,152 A * 12/1999 Lynch .......................... 435/7.1
6,197,527 B1 * 3/2001 Lynch et al.

OTHER PUBLICATIONS

Andersen, A.H., et al., "Topoisomerase I has a strong binding preference for a conserved hexadecameric sequence in the promoter region of the rRNA gene from tetrahymena pyriformis", *Nucleic Acids Research*, 13 (5), pp. 1543–1557, (1985).
Bonven, B.J., et al., "A High Affinity Topoisomerase I Binding Sequence Is Clustered at DNAase I Hypersensitive Sites in Tetrahymena R–Chromatin", *Cell*, 41, pp. 541–551, (Jun. 1985).
Burgin, Jr., A.B., et al., "A novel suicide substrate for DNA topoisomerases and site–specific recombinases", *Nucleic Acids Research*, 23 (15), pp. 2973–2979, (1995).
Chakraborty, A.K., et al., "Mode of Action of Pentavalent Antimonials : Specific Inhibition of Type I DNA Topoisomerase of Leishmania Donovani", *Biochemical and Biophysical Research Communications*, 152 (2), pp. 605–611, (Apr. 29, 1988).
Fan, Y., et al., "Molecular Modeling Studies of the DNA–Topoisomerase I Ternary Cleavable COmplex with Camptothecin", *J. Med. Chem.*, 41, pp. 2216–2226, (1998).
Hwang, Y., et al., "DNA Contacts by Protein Domains of the Molluscum Contagiosum Virus Type–1B Topoisomerase", *Virology*, 262, pp. 479–491, (1999).
Hwang, Y., et al., "DNA Contacts Stimulate Catalysis by a Poxvirus Topoisomerase", *The Journal of Biological Chemistry*, 274 (14), pp. 9160–9168, (1999).
Hwang, Y., et al., "Mechanism of Inhibition of a Poxvirus Topoisomerase by the Marine Natural Product Sansalvamide A", *Molecular Pharmacology*, 55, pp. 1049–1053, (1999).
Hwang, Y., et al., "Mulluscum Contagiosum Virus Topoisomerase: Purification, Activities, and Response to Inhibitors", *Journal of Virology*, 72 (4), pp. 3401–3406, (Apr. 1998).
Jaxel, C., et al., "Effect of Local DNA Sequence on Topoisomerase I Cleavage in the Presence or Absence of Camptothecin", *The Journal of Biological Chemistry*, 266 (30), pp. 20418–20423, (Oct. 25, 1991).
Kono, S., et al., "A Case–Control Study of Gastric Cancer and Diet in Northern Kyushu, Japan", *Jpn. J. Cancer Res. (Gann.)*, 79, pp. 1067–1074, (Oct. 1998).
Pommier, Y., et al., "Mechanism of action of eukaryotic DNA topoisomerase I and drugs targeted to the enzyme", *Biochimica et Biophysica Acta*, 1400, pp. 83–106, (1998).
Pouliot, J.J., et al., "Yeast Gene for a Tyr–DNA Phosphodiesterase that Repairs Topoisomerase I Complexes", *Science*, 286, pp. 552–555, (Oct. 15, 1999).
Redinbo, M.R., et al., "Crystal Structures of Human Topoisomerase I in Covalent and Noncovalent Complees with DNA", *Science*, 279, pp. 1504–1513, (Mar. 6, 1998).
Redinbo, M.R., et al., "Structural insights into the function of type IB topoisomerases", *Current Opinion in Structural Biology*, 9, pp. 29–36, (1999).
Richet, E., et al., "Synapses of Attachment Sites during Lambda Integrative Recombination Involves Capture of a Naked DNA by a Protein–DNA Complex", *Cell*, 52, pp. 9–17, (Jan. 15, 1988).
Shuman, S., "DNA Strand Transfer Reactions Catalyzed by Vaccinia Topoisomerase I", *The Journal of Biological Chemistry*, 267 (12), pp. 8620–8627, (Apr. 25, 1992).
Shuman, S., "Vaccinia virus DNA topoisomerase : a model eukaryotic type IB enzyme", *Biochimica et Biophysica Acta*, 1400, pp. 322–337, (1998).
Stewart, L., et al., "A Model for the Mechanism of Human Topoisomerase I", *Science*, 279, pp. 1534–1541, (Mar. 6, 1998).
Tajima, K., et al., "Dietary Habits and Gastro–Intestinal Cancers: A Comparative Case–Control Study of Stomach and Large Intestinal Cancers in Nagoya, Japan", *Jpn. J. Cancer Res. (Gann.)*, 76 (8), pp. 705–716, (Aug. 1985).
Taniguchi, S., et al., "Effect of (–)–epiallocatechin gallate, the main constituent of green tea, on lung metastasis with mouse B16 melanoma cell lines", *Cancer Letters*, 65, pp. 51–54, (1992).
Tanizawa, A., et al., "Induction of cleavage in topoisomerase I c–DNA by topoisomerase I enzymes from calf thymus and wheat germ in the presence and absence of camptothecin", *Nucleic Acids Research*, 21 (22), pp. 5157–5166, (1993).
Yamane, Y., et al., "Inhibition of N–Methyl–N'–nitro–N–nitrosoguanidine–induced Carcinogenesis by (–)–Epigallocatechin Gallete in the Rat Glandular Stomach", *Cancer Research*, 55, pp. 2081–2084, (May 5, 1995).

* cited by examiner

Primary Examiner—Gary Benzion
Assistant Examiner—Arun K. Chakrabarti
(74) Attorney, Agent, or Firm—McDermott, Will & Emery

(57) ABSTRACT

The present invention provides methods for screening compounds capable of modulating nucleic acid-modifying enzymatic activity, including topoisomerase activity.

18 Claims, 11 Drawing Sheets

A.

METHOD OF IDENTIFYING INHIBITORS OF TOPOISOMERASE DNA RELIGATION

The invention was made with the support of NIH Grant No. R01 AI46222. The U.S. government has certain rights in the invention.

BACKGROUND OF THE INVENTION

There is an increasing concern in the medical community regarding the emergence of strains of bacteria and other pathogens that are resistant to known antibiotics. Scientists, therefore, are attempting to discover new therapies that are effective through novel modes of action.

The topoisomerase family of enzymes is a target for several important anti-tumor and anti-infective drugs (A. Kornberg and T. Baker. 1991. *DNA Replication* (W. H. Freeman and Company, New York); Y. Pommier, P. Pourquier, Y. Fan and D. Strumberg. 1998. Mechanism of action of eukaryotic DNA topoisomerase I and drugs targeted to the enzyme. *Biochim. Biophys. Acta* 1400, 83–106). Topoisomerases are ubiquitous and essential enzymes in cells. By introducing transient breaks into the helix, topoisomerases relax the DNA superhelical tension that arises in cells as a result of several nuclear processes including DNA replication, transcription, chromatin assembly, recombination, and chromosome segregation. The breaks that they generate may be single or double-stranded breaks, depending on the specific type of topoisomerase.

Compounds that act as effective cellular inhibitors of topoisomerases are expected to act as cytotoxic agents through the disruption of the normal cell division process. Such agents that are sufficiently potent and selective will be of great use as antibacterial and antifungal agents. Topoisomerases are also encoded by the genetic material in certain viruses, so development of topoisomerase inhibitors that are effective against viral topoisomerases may provide effective antiviral agents. Further, because cell division is an important characteristic of cancers and other proliferative diseases, agents that inhibit topoisomerases will also be useful as antineoplastic agents.

Many inhibitors trap the covalent topoisomerase-DNA intermediate, leading to the persistence of DNA breaks that disrupt cell growth. For example, amptothecin traps covalent intermediates made by human topoisomerase IB and thereby kills rapidly dividing cancer cells. The anti-Leishmania effect of pentavalent antimonials has been proposed to be a result of inhibiting the parasitic topoisomerase IB (A. K. Chakraborty and H. K. Majumder. 1988. Mode of action of pentavalent antimonials: specific inhibition of type I DNA topoisomerase of *Leishmania donovani*. *Biochem. Biophys. Res. Commun.* 152, 605–611). The marine natural product sansalvamide A1 was recently found to inhibit the topoisomerase of the pathogenic poxvirus molluscum contagiosum (MCV) (Y. Hwang, D. Rowley, D. Rhodes, J. Gertsch, W. Fenical and F. D. Bushman. 1999. Mechanism of inhibition of a poxvirus topoisomerase by the marine natural product sansalvamide A. *Mol. Pharmacol.* 55, 1049–1053). Emphasizing the toxicity of trapped covalent intermediates is the recent discovery of a DNA repair pathway dedicated solely to removing stalled intermediates from cellular DNA (J. J. Pouliot, K. C. Yao, C. A. Robertson and H. A. Nash. 1999. Yeast Gene for a Tyr-DNA Phosphodiesterase that Repairs Topoisomerase I Complexes. *Science* 286, 552–555).

Although previous methods for detecting topoisomerase inhibitors have been available, (see, e.g., Andrea et al., (1991) *Mol. Pharmacol.* 40(4):495–501; Muller et al., *Nucleic Acids Res.* 17(22):9499; Lynch et al., U.S. Pat. No. 5,998,152), the search for effective inhibitors for topoisomerases has been difficult due to the fact that a good screening assay does not exist. Previously available assays were not amenable to high throughput screening methods such as are needed to screen large libraries or groups of potential inhibitors. The known gel-based assays for topoisomerase function are not convenient for monitoring large numbers of tests. Other previously available assays required multiple steps or reagents. Prior assays required multiple steps that often identified compounds with non-specific characteristics, which often required further evaluation to determine its activity, e.g., whether the compound inhibited formation or trapping of covalent complexes. In addition, previously available assays employed reagents that often tainted or distorted the results of the assay or compound. For example, denaturants were often employed that disrupted enzymatic activity of the topoisomerase. Also, many of the currently available assays require the use of radioactive compounds and/or suffer from a lack of sensitivity. Thus, there remains a continuing need for high-throughput screening assays for inhibitors active against topoisomerases. There also remains a need for a method of treating infectious diseases and cancers by administering a topoisomerase inhibitor.

SUMMARY OF THE INVENTION

The present invention provides high-throughput methods of screening compounds capable of modulating topoisomerase activity by incubating at least a first nucleic acid, a topoisomerase and a potential topoisomerase-modulating compound, wherein the nucleic acid is operatively associated with at least one tag, and assaying for nucleic acid religation. It is then possible to measure the level of substrate nucleic acid religation activity in the presence and absence of the topoisomerase-modulating compound, wherein the level of religation activity is inversely proportional to the effectiveness of the topoisomerase-inhibitory compound. The nucleic acid may be single-stranded or double-stranded DNA, or single-stranded or double-stranded RNA. The tag may be a detection tag or an affinity tag. The method may involve incubating at least a first nucleic acid and a second nucleic acid, and the first nucleic acid may be operatively associated with an affinity tag, and the second nucleic acid may be operatively associated with a detection tag. The topoisomerase-modulating compound may be a topoisomerase inhibitor or an activator. The topoisomerase may be a Type I, Type II, Type III or Type IV topoisomerase. The screening assay may be performed on a solid support or in a liquid phase. The nucleic acid and topoisomerase may be covalently complexed, wherein the topoisomerase retains its religation activity.

The present invention also provides methods of treating cancer or an infection by a pathogen by administering a pharmaceutical composition including a topoisomerase inhibitor to a patient in need thereof. The pathogen may be a virus, bacterium, fungus or parasite.

The present invention further provides a kit for screening compounds that modulate topoisomerase religation activity that contains (a) a substrate nucleic acid having a first tag, (b) a religation nucleic acid having a second tag, (c) a topoisomerase, and (d) a means for measuring nucleic acid religation activity of a test mixture including (a), (b) and (c) in the presence or absence of a topoisomerase-modulating compound.

The present invention also provides a high-throughput method of screening compounds capable of modulating nucleic acid-modifying enzymatic activity by incubating at least a first nucleic acid, a nucleic acid-modifying enzyme and a potential enzyme-modulating compound, wherein the nucleic acid has at least one tag, and assaying for nucleic acid religating or cleavage.

B. DNA sequence of substrates for MCV-TOP and EU-TOPO. The arrows indicate the points of cleavage in the covalent intermediate. Topoisomerase recognition sites are underlined. "B" indicates biotin, "DIG" indicates digoxigenin modifications. "HW" numbers indicate the names of oligonucleotide strands. MCV sub a': MCV-TOP substrate set. EU TG: mammalian type IB topoisomerase substrate, containing TG nucleotides flanking the point of cleavage. EU TG+P: same as EU TG substrate but containing a 5' phosphate on strand HW410 to block self-religation hairpin formation. EU TA+P: same as EU TG+P except an A/T base pair is substituted for G/C 3' of the point of cleavage.

C. Diagram of the method for detecting religation product. "A" indicates avidin molecules bound to a microtiter plate. "Ab" and "P" indicate the antibody peroxidase conjugate. "TMB" indicates the 3,3'-5,5'-tetramethylbenzidine peroxidase substrate. After the topoisomerase reaction, the product mixture was added to avidin-coupled microtiter wells. Unbound DNA was removed by washes. Bound DNA was then quantitated by detecting digoxigenin using an anti-DIG ELISA.

Figure 3:
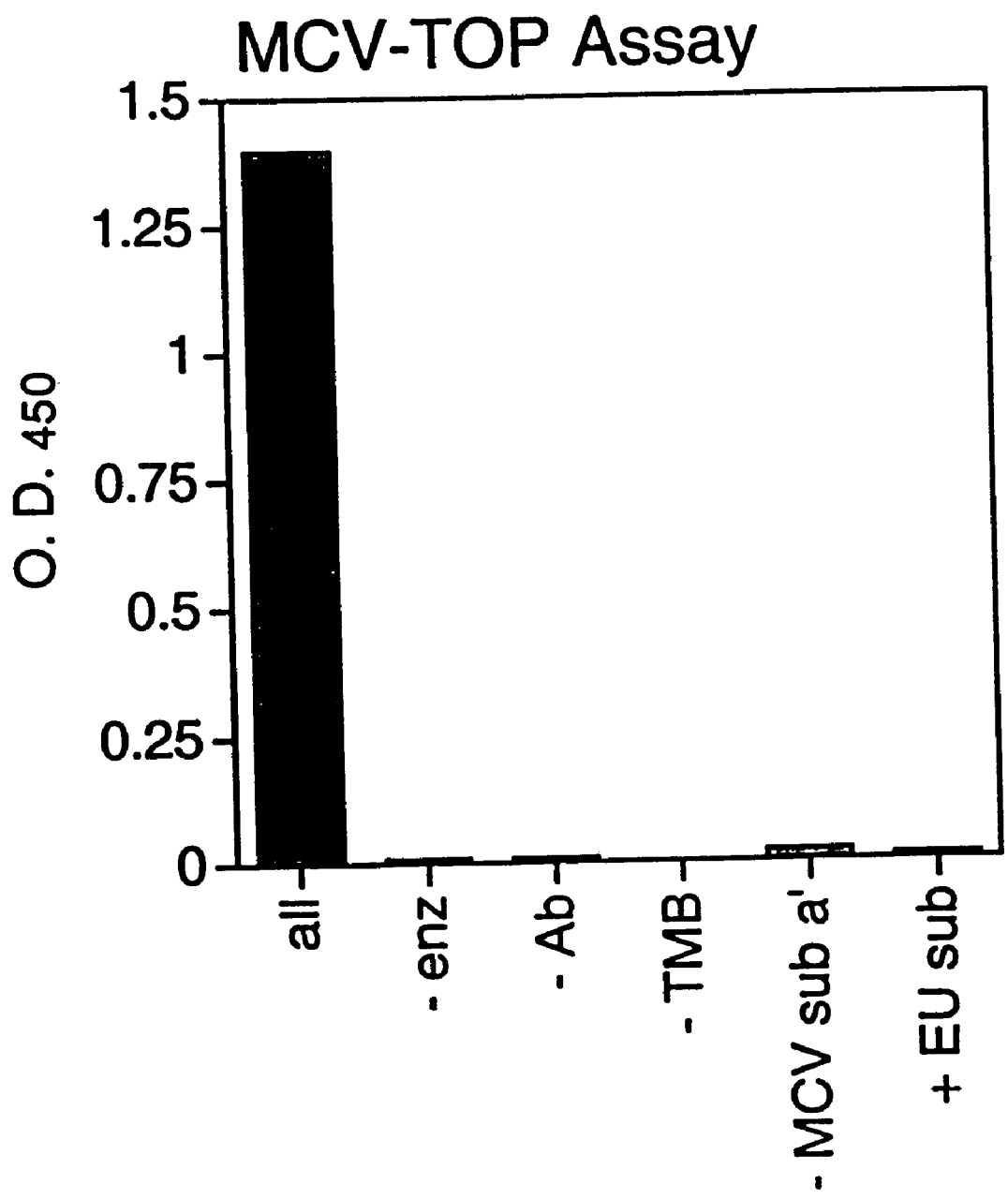

FIG. 3. Requirements for the microtiter assay of MCV-TOP activity. Reactions contained the complete set of reagents ("all") or lacked the indicated ingredient (−). In the right most lane (+EU sub), the EU TG+P substrate was substituted for MCV sub a'. All reactions were repeated at least three times.

FIG. 4. Assays of EU-TOPO activity. A. Diagram of formation of the self-religated hairpin products. DNA strands are indicated by the thick lines, the ball marked "TOP" indicates EU-TOPO, and the asterisk indicates the point of 5' end labeling.

B. Requirements for the EU-TOPO microtiter assay. Reactions contained the complete set of reagents ("all") or lacked the indicated ingredient (−). In the right most lane (+MCV sub a'), the MCV sub a' substrate was substituted for EU TG+P. All reactions were repeated at least three times.

Figure 5:
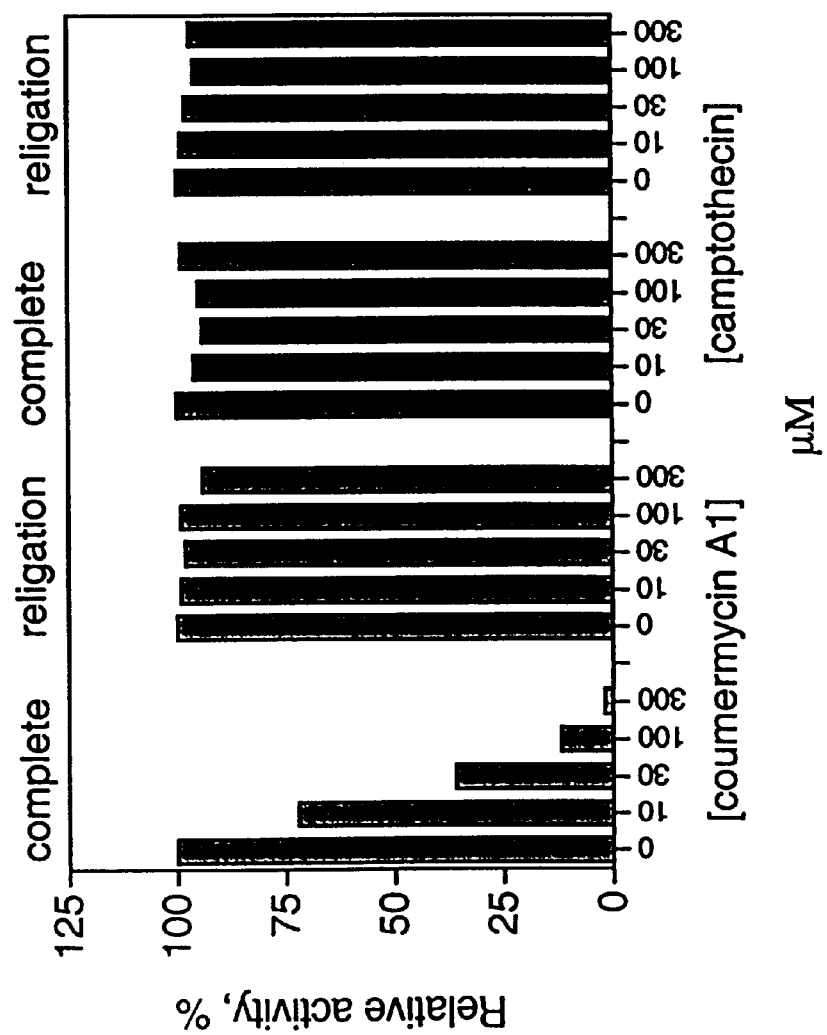
Figure 5:
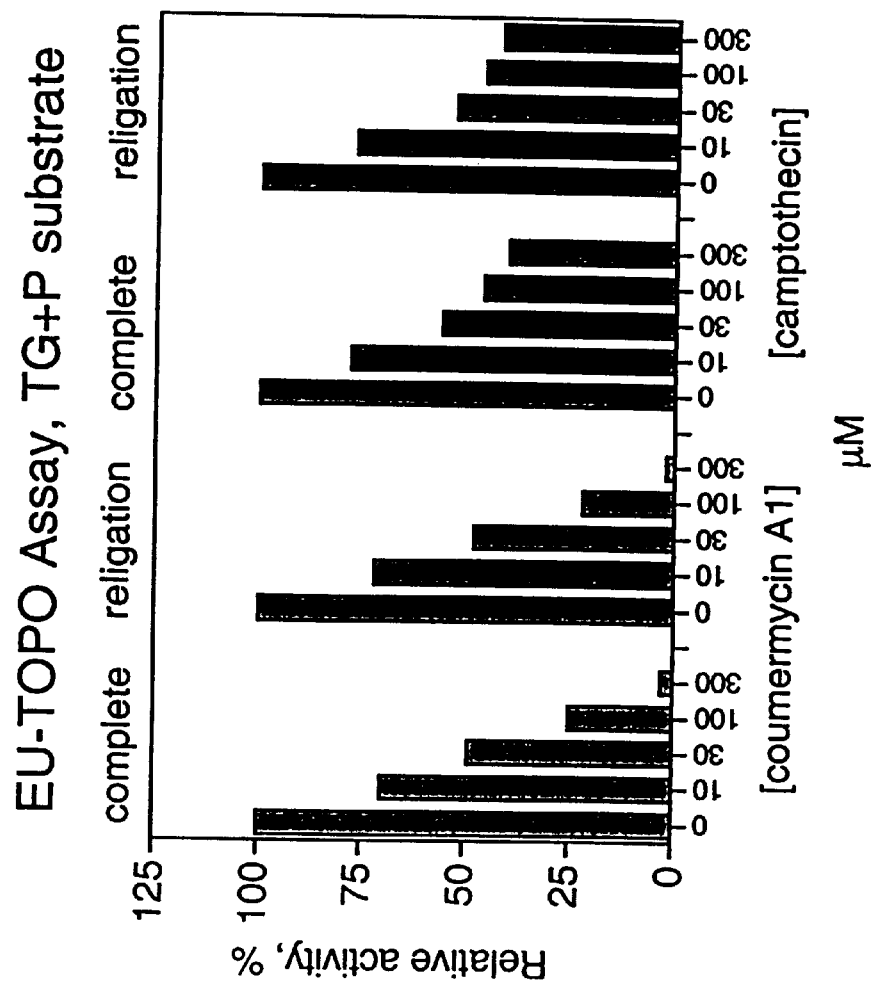
Figure 5:
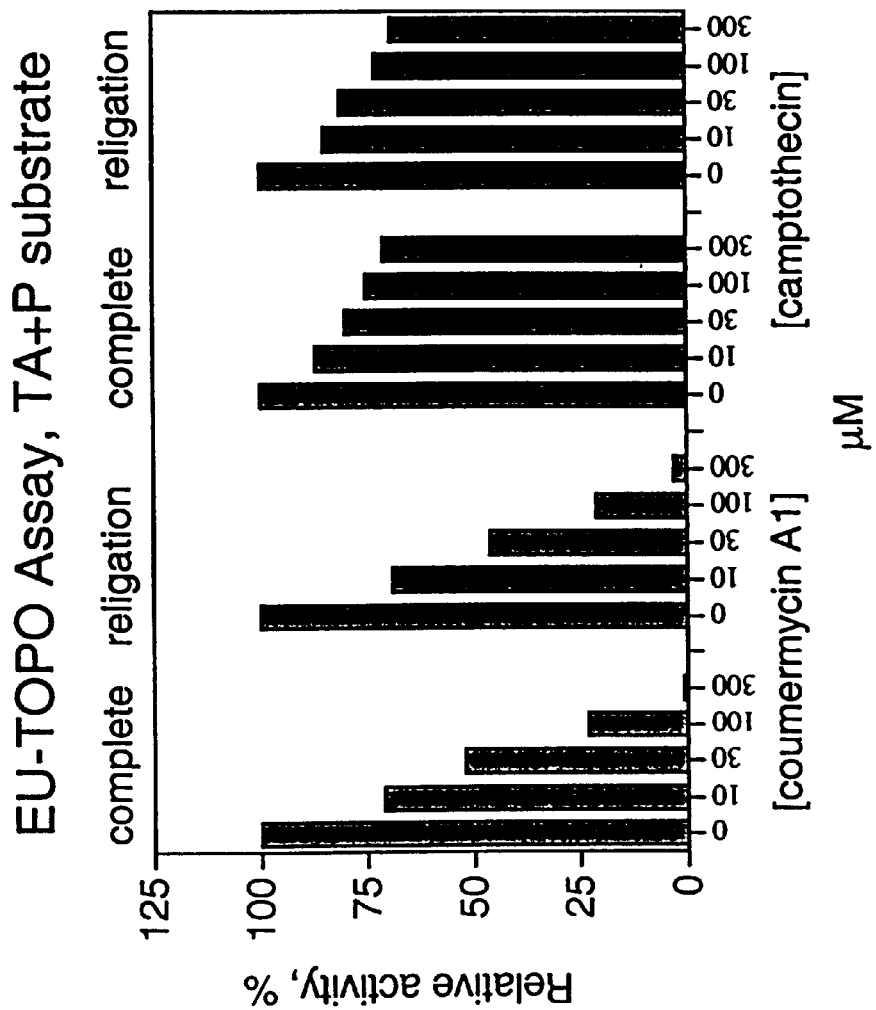

FIG. 5. Inhibition of MCV-TOP and EU-TOPO by coumermycin A1 and camptothecin. "Complete" indicates that the inhibitor was added to the topoisomerase before addition of substrate, thereby assaying for inhibition at any step in the reaction. "Religation" indicates that the inhibitor was added after covalent complex formation, thus assaying inhibition of the religation step. Concentrations in micromolar are shown at the bottom. Assays were normalized to the uninhibited control (100% activity). Measurements were repeated at least ten times. A. Assays of MCV-TOP. B. Assays of EU-TOPO using EU TG+P substrate. C. Assays of EU-TOPO using EU TA+P substrate.

Figure 6:
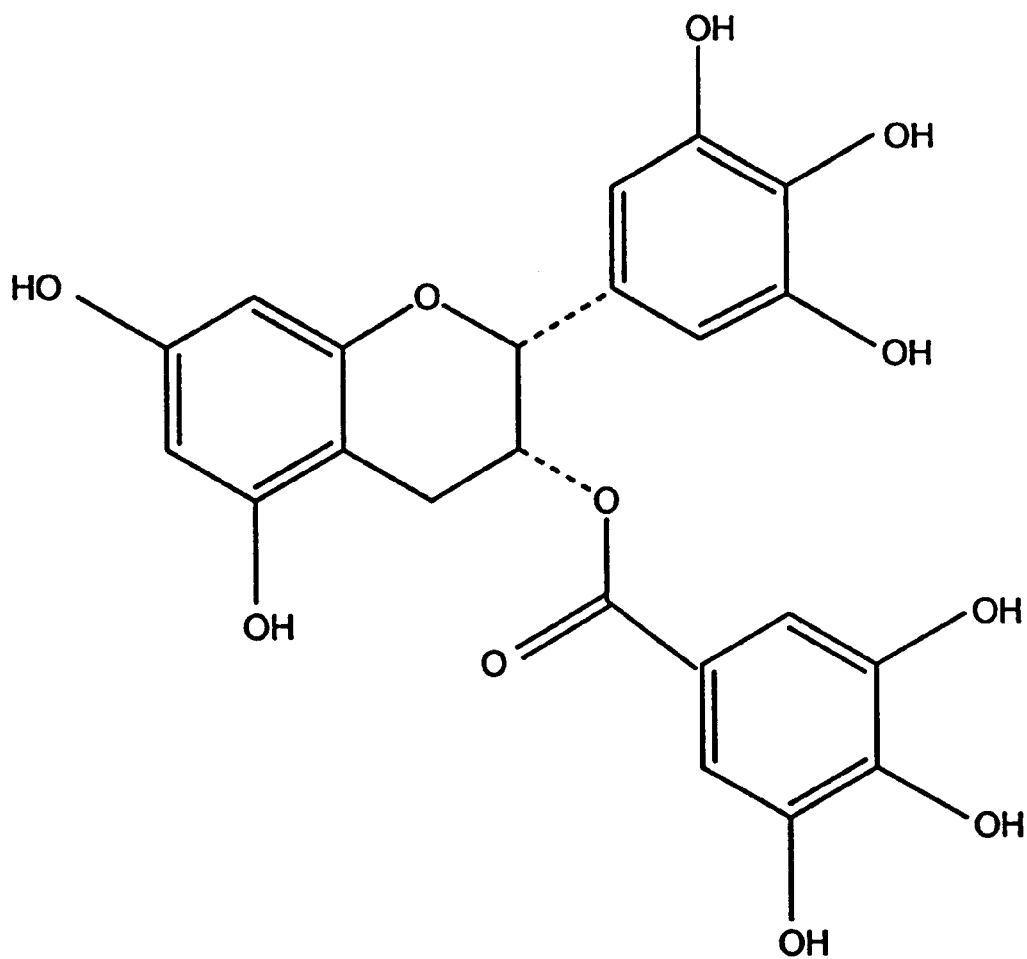
Figure 6:
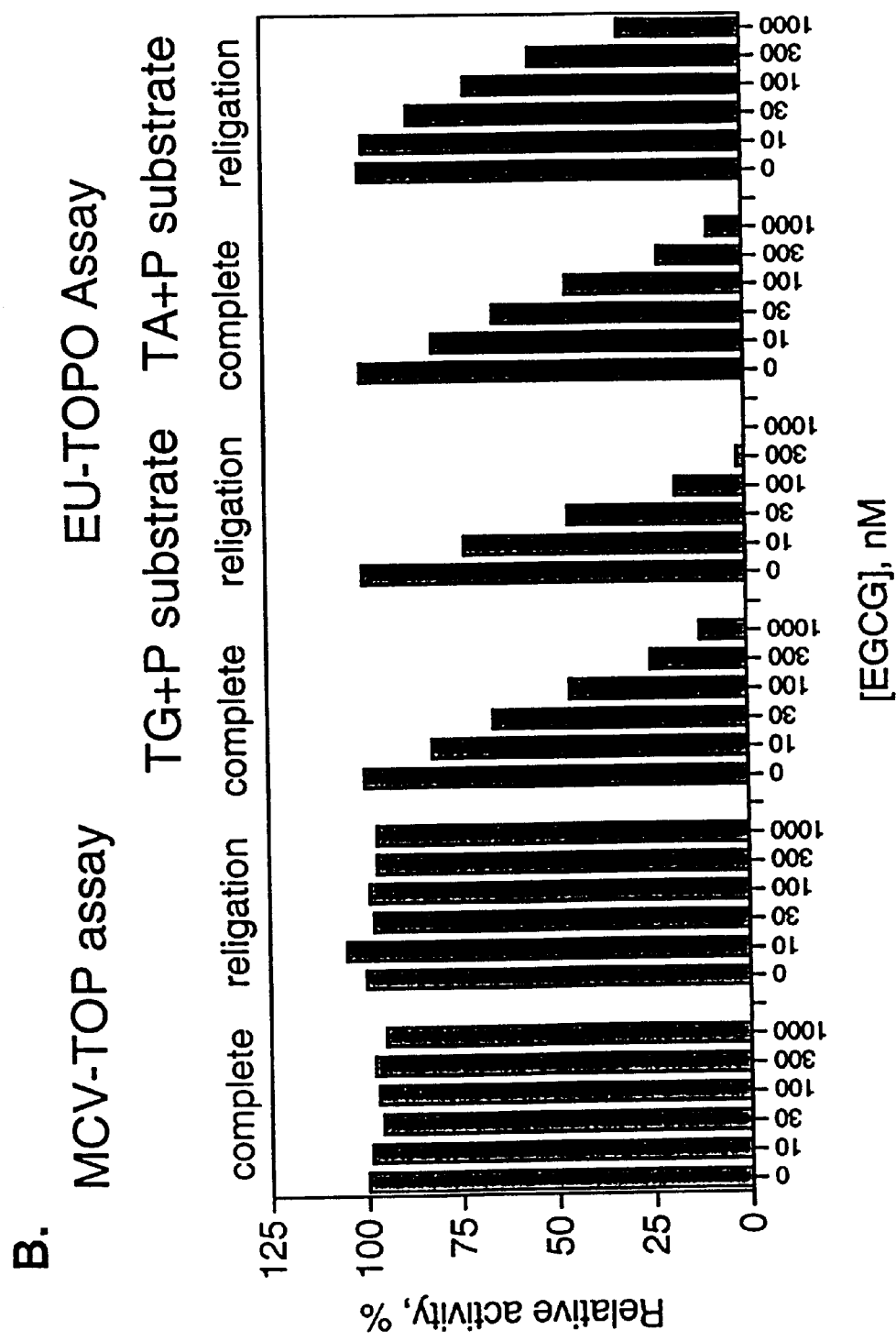

FIG. 6. Potent inhibition of EU-TOPO by EGCG. A. Structure of EGCG. B. Assays of EU-TOPO in the presence of different concentrations of EGCG. Figure labels for FIG. 6 are as in FIG. 5 except the inhibitor concentrations are in nanomolar.

DETAILED DESCRIPTION OF THE INVENTION

The present invention provides methods for identifying topoisomerase activity modulators. In general, solid phase and liquid phase assay formats are employed to measure the activity of a topoisomerase in the presence of a potential topoisomerase activity modulator(s). High-throughput screening (HTS) methods, compositions, kits and integrated systems for performing he assays are also provided. In a particular aspect of the present invention, the assays are performed by contacting a tagged substrate nucleic acid with a topoisomerase in an appropriate reaction mixture that also includes a potential modulator of topoisomerase activity and a religation strand, preferably having a second tag. The presence or absence of a substrate nucleic acid-religation strand complex is then detected to ascertain whether a modulator of topoisomerase activity was present in the reaction mixture. For example, if the potential topoisomerase activity modulator is a topoisomerase inhibitor, i.e., which causes "trapping" of the topoisomerase in a covalent complex with the substrate nucleic acid, the religation strand will not ligate to the substrate nucleic acid.

Topoisomerase modulators identified by use of the assays have value for in vitro modification of topoisomerase activity, e.g., as tools for recombinant methods, cell culture modulators, and the like. More important, these assays are useful for detecting topoisomerase enzyme inhibitors that provide lead compounds for drug development of a variety of conditions, including antibacterial, antifungal, antiviral or anti-neoplastic agents. See, for example, Drlica et al. (1997) *Microbiol. Mol. Biol. Rev.* 61:377–392; Wang (1996) *Ann. Rev. Biochem.* 65:635–692; Froelich-Ammon et al. (1995) *J. Biol. Chem.* 270:21429–21432; Roca et al. (1994) *Proc. Nat. Acad. Sci. U.S.A.* 91:1781–1785; Maxwell (1993) *Mol. Microbiol.* 9:681–686; Sorensen et al. (1992) *J. Mol. Biol.* 228:778–786; Reece et al. (1991) *Crit. Rev. Biochem. Mol. Biol.* 26:335–375. Accordingly, the assays are of immediate value for their ability to identify lead compounds for pharmaceutical or other applications.

Indeed, because topoisomerases play a central role in nucleic acid metabolism and thus are important in a variety of biological processes related to cell division, DNA replication, chromosome structure (condensation, segregation, and partition) and gene expression, modulators identified by the assays of the invention are leads for a variety of conditions, including neoplasia, viral infection, bacterial infection fungal infection, and the like (see, e.g., Kato and Kikuchi, (1998) *Nagoya J. Med. Sci.* 61(1–2):11–26; Roca J (1995) *Trends Biochem. Sci.* 20(4):156–60; Wigley D B (1995) *Annu. Rev. Biophys. Biomol. Struct.* 24:185–208). In addition, topoisomerase modulators that specifically target undesired organisms, such as viruses, fungi, agricultural pests, or the like, can serve as fungicides, bactericides, herbicides, insecticides, etc. Thus, the range of conditions that topoisomerase activity modulators are applicable to include conditions in humans and other animals, and in plants, e.g., for agricultural applications.

The invention represents an improvement over existing technology in several ways. Through the use of different nucleic acid substrate, one can adapt the assays of the invention to screen for inhibitors of numerous different classes of topoisomerase enzymes, including those that may demonstrate sequence-specific nucleic acid binding properties; one can assay multiple different topoisomerase enzymes in a single reaction, thus enhancing assay throughput; the assays can be run in a parallel fashion such that multiple different topoisomerase enzymes and/or modulators are assayed simultaneously; the assay format does not require that the enzyme be immobilized on a solid support during the course of the assay; assays can be performed in the liquid or solid-phase and each of the formats described is readily amenable for automation and HTS using current reagents, devices and methodologies.

Further, the assays are extremely sensitive relative to previously described assay formats, and only minimal quantities of the necessary reagents are required. Typically, the enzyme is present in a range of about 1–100 nM, so in cases in which topoisomerase availability is limiting, these assay formats have a significant advantage over previously known topoisomerase assays. Also, the substrate nucleic acid and religation strand can be quite short, which makes the assay formats economical.

Topoisomerases

The assays are useful for identifying modulators of many different topoisomerases. Topoisomerases are reviewed in, for example, Wigley, D. B. (1995) *Ann. Rev. Biophys. Biomolec. Struct.* 24: 185–208 and Bjornsti and Osheroff, DNA Topoisomerases Protocols: Enzymology and Drugs (Humana Press, 1999). The assay methods are useful for identifying activity modulators of, for example, Type I DNA topoisomerases (EC 5.99.1.2; also known as relaxing enzyme, untwisting enzyme, swivelase, nicking-closing enzyme, and omega-protein). The Type I DNA topoisomerases can convert one topological isomer of DNA into another, e.g. these topoisomerases can relax superhelical turns in DNA, interconvert simple and knotted rings of single-stranded DNA, and intertwist of single-stranded rings of complementary sequences. Type I topoisomerases act by catalyzing the transient breakage of DNA, one strand at a time, and the subsequent rejoining of the strands. In the process of breaking the strand, a Type I topoisomerase simultaneously forms a topoisomerase-DNA link in which the hydroxyl group of a tyrosine residue is joined to a 5'-phosphate on DNA, at one end of the enzyme-severed DNA strand. Sources of Type I topoisomerases include both prokaryotes and eukaryotes; examples of Type I topoisomerases include bacterial topoisomerases I and III, fungal topoisomerases I and III, human topoisomerases I, IIIα and IIIβ, as well as Type I viral topoisomerases such as molluscum contagiosum virus type-1B topoisomerase (Hwang et al. *Virology* (1999) 262(2):479–91 and Hwang et al. *J Virol.* (1998)72(4):3401–6. Some Type I topoisomerases are commercially available (e.g., calf thymus topoisomerase I, *Drosophila melanogaster* topoisomerase I, human topoisomerase I, and vaccinia topoisomerase I).

The assays are also applicable to modulators of Type II DNA topoisomerases (EC 5.99.1.3; also known as DNA topoisomerase II and DNA gyrase). The Type II DNA topoisomerases can change the topology of double-stranded DNA molecules, causing, for example, the relaxation of supercoiled DNA molecules, catenation, decatenation, knotting and unknotting of circular DNA (for review, see Berger J M (1998) *Curr. Opin. Struct. Biol.* 8(1):26–32; Watt and Hickson (1994) *Biochem. J.* 303:681–695). Type II topoisomerases act by a concerted breakage and reunion activity involving both strands of the DNA duplex. This activity is absolutely required for DNA replication and transcription. The active species of bacterial type II topoisomerases is a heterotetramer consisting of, for the DNA gyrases, two "A" (or "α") subunits and two "B" (or "β") subunits (Tsai-Pflugfelder et al. (1988) *Proc. Nat'l. Acad. Sci. USA* 85: 7177–81; Jenkins et al. (1992) *Nucleic Acids Res.* 20:5587–92), commonly referred to as GyrA and GyrB, respectively. Topoisomerase IV, which is a type II topoisomerase found in bacteria, comprises two subunits, ParC and ParE. The ParC subunit is homologous to the gyrase A protein, while the ParE subunit is homologous to the gyrase B subunit (Kato et al. (1990) *Cell* 63: 393–404; published erratum appears in *Cell* (1991) 65:1289). The GyrA or ParC subunit catalyzes breaking and rejoining of the DNA strands, while the GyrB or ParE subunit catalyzes ATP hydrolysis. Examples of Type II topoisomerases include, for example, bacterial topoisomerases II and IV, fungal topoisomerase II, human topoisomerases IIα and IIβ as well as Type II viral topoisomerases.

Other types of topoisomerases can also be used in the assays of the invention. For example a cDNA encoding human DNA topoisomerase III has been cloned and sequenced (Hanai et al. (1996) *Proc. Nat. Acad. Sci.* 93:3653–3657). DNA topoisomerase III protein is homologous to the *E. coli* DNA topoisomerase I subfamily of enzymes, but shares no significant sequence homology with eukaryotic DNA topoisomerase I. Topoisomerase III catalyzes the reduction of supercoils in highly negatively supercoiled DNA.

In the assays of the invention, preferred topoisomerases are typically selected from medically relevant sources such as human topoisomerases I, IIα, IIβ, IIIα and IIIβ (e.g., for assays designed to identify compounds that modulate cell growth, or for inhibition of neoplasia); or from infectious organisms such as infectious fungi, e.g., Aspergillus, Candidia species; bacteria, particularly *E. coli*, which serves a model for pathogenic bacteria, as well as medically important bacteria such as Staphylococci (e.g., *aureus*), Streptococci (i.e., *pneumoniae*), Clostridia (e.g., *perfringens*), Neisseria (e.g., *gonorrhoea*), Enterobacteriaceae (e.g., *coli*), Helicobacter (e.g., *pylori*), Vibrio (e.g., *cholerae*), Capylobacter (e.g., *jejuni*), Pseudomonas (e.g., *aeruginosa*), Haemophilus (e.g., *influenzae*), Bordetella (e.g., *pertussis*), Mycoplasma (e.g., *pneumoniae*) Ureaplasma (e.g., *urealyticum*), Legionella (e.g., *pneumophila*), Spirochetes (e.g., Trepnema, Leptospira and Borrelia), Mycobacteria (e.g., *tuberculosis, smegnatis*), Actinomyces (e.g., *israelii*) Nocardia (e.g., *asteroides*), Chlamydia (e.g., *trachomatis*), Rickettsia, Coxiella, Ehrilichia, Rochalimaea, Brucella, Yersinia, Fracisella, and Pasteurella; protozoa such as sporozoa (e.g., Plasmodia) *rhizopods* (e.g., Entamoeba) and flagellates (Trypanosoma, Leishmania, Trichomonas Giardia, etc.); viruses such as the (+) RNA Poxviruses (e.g., *vaccinia*) viruses and certain other dsDNA viruses (e.g., African Swine Fever Virus). Other assays are designed to be relevant to non-medical uses, such as assays for inhibitors for topoisomerases from crop pests such as insects, fungi, weed plants, and the like. Preferred topoisomerase include human topoisomerases I, IIα, IIβ, IIIα and IIIβ and bacterial topoisomerases I, II, III and IV.

Topoisomerases may be purified from a natural source or may be recombinantly produced, and are usually provided in at least a partially-purified form, although the assays can function when provided with a crude cell lysate that contains a topoisomerase. In a preferred embodiment, the topoisomerases are synthesized using recombinant DNA methodology. Generally this involves creating a DNA sequence that encodes the topoisomerase, modified as desired, placing the DNA in an expression cassette under the control of a particular promoter, expressing the protein in a host, isolating the expressed protein and, if required, renaturing the protein. Topoisomerases, and nucleic acids encoding topoisomerases that are useful for recombinant production of topoisomerases for use in the assays of the invention, and methods of obtaining such topoisomerases and nucleic acids encoding same, are known to those of skill in the art (see, e.g., Lynch et al. U.S. Pat. No. 5,998,152 and Bjornsti and Osheroff, *DNA Topoisomerases Protocols: Enzymology and Drugs* (Humana Press, 1999)).

Occasionally only a portion of a native topoisomerase is used in the assay, the portion being sufficient for topoisomerase activity of preferably not less than an order of magnitude less than that of the full-length topoisomerase. Portions capable of imparting the requisite binding specificity and affinity, and/or the religation activity, are readily identified by those skilled in the art (e.g., Champoux J J, *Prog. Nucleic Acid Res. Mol. Biol.* (1998) 60:111–32). For example, substrate nucleic acid can be covalently complexed with an active religation domain of topoisomerase. A wide variety of molecular and biochemical methods are available for generating catalytic fragments of a topoisomerase.

Reaction mixtures for the assays are such that topoisomerases are catalytically active. Prokaryotic type I topoisomerases require $Mg^{2+}$ (generally 1–5 mM $MgCl_2$), while eukaryotic type I topoisomerases generally do not require $Mg^{2+}$. Type I topoisomerases do not require any high energy cofactor, while some reactions of Type II topoisomerases utilize ATP. Topoisomerases are active across a relatively broad pH range, with an optimum in conventional Tris buffers of 7.6 for Type I topoisomerases and 7.5–9.0 in Type II topoisomerases. Reactions can also include one or more of a reducing agent (e.g., 2–5 mM dithiothreitol), a condensing agent (e.g., 5 mM spermidine), and an inert enzyme stabilizer (e.g., BSA).

Solid Phase Assays

In the solid phase assays of the invention, an effect of a potential topoisomerase activity modulator on the activity of a DNA topoisomerase is determined by detecting the presence of a substrate nucleic acid-religation strand complex. The complex is immobilized prior to detection. The solid phase topoisomerase modulation assays provided by the invention use an oligonucleotide substrate as the substrate nucleic acid.

Assays Employing Oligonucleotide Substrates

An embodiment of the solid phase topoisomerase assay involves the use of an oligonucleotide as the substrate for the topoisomerase. A test reaction mixture is made that includes a topoisomerase, a substrate nucleic acid comprising a first tag, a potential activity modulator and a religation strand that is linked to a second tag. The topoisomerase and substrate nucleic acid can alternatively be provided in the assay as a covalent complex formation (see, e.g., Hwang et al. *Mol. Pharmacol.* (1999) 55(6):1049–53). The mixture is incubated for a suitable period of time under conditions appropriate for topoisomerase activity. A solid support is also provided, to which the first tag is bound, thus binding the tagged substrate nucleic acid to the solid support. The solid support is then washed, preferably in a high salt solution, and then assayed to determine whether the substrate nucleic acid and the religation strand have religated. Religation of the religation strand to the substrate nucleic acid can be detected directly by detection of the second tag. For example, the solid support-bound nucleic acid (i.e., the complex comprising the religated substrate-religation strand, or the religated nucleic acid) is contacted with a detection moiety that binds to the second tag or the second tag can be a detection tag. By detecting the presence or absence of the detection tag on the solid support, one can determine whether the potential activity modulator has had an effect on topoisomerase activity. Only if the topoisomerase has ligated the religation strand to the substrate nucleic acid will the detection tag be able to indirectly bind to the bound religated nucleic acid.

An alternative embodiment of the solid phase topoisomerase assay invloves the use of a test reaction mixture that includes a topoisomerase, a substrate nucleic acid comprising a first tag at one end of the nucleic acid and a second tag at the other end of the molecule, and a potential activity modulator. The mixture is incubated for a suitable period of time under conditions appropriate for topoisomerase activity. A solid support is also provided, to which the substrate nucleic acid is bound either before or after the incubation step. The solid support is then washed, preferably in a high salt solution, and then assayed to determine whether the substrate nucleic acid and the religation strand have religated. In this embodiment, the "religation strand" is simply a portion of the original nucleic acid that was first cleaved by the topoisomerase. If the activity modulator inhibits the topoisomerase, the religation strand will not be religated to the substrate molecule, and will be washed away during the washing step. Therefore, the loss of one of the tags is determinative of an effective topoisomerase inhibitor.

Nucleic acids used in this type of assay format, either the substrate nucleic acid or the religation strand, can be any polynucleotide recognized by a topoisomerase. Such polynucleotides can include single-stranded RNA, a double-stranded RNA, a single-stranded DNA, a double-stranded DNA, a double-stranded DNA-RNA hybrid, an RNA analogue, and a DNA analogue. The particular topoisomerase being assayed can influence the choice of oligonucleotide employed for the assay. Those of skill in the art will readily recognize oligonucleotides that can be employed for particular topoisomerases. (See, e.g., Capranico and Binaschi, *Biochim. Biophys. Acta.* (1998) 1400(1–3):185–94; Hwang et al. *Virology* (1999) 262(2):479–91). For example, a Type II topoisomerase requires a double-stranded oligonucleotide substrate and religation strand, while a Type I topoisomerase can use either single- or double-stranded nucleic acids.

Most commonly, this assay format uses oligonucleotides that are made synthetically. Synthetic oligonucleotides are typically synthesized chemically according to common solid phase phosphoramidite triester methods described, e.g., by Beaucage and Caruthers (1981) *Tetrahedron Letts.* 22(20):1859–1862, e.g., using an automated synthesizer, as described in Ncedham-VanDevanter et al. (1984) *Nucleic Acids Res.* 12: 6159–6168. Oligonucleotides can also be custom made and ordered from a variety of commercial sources known to persons of skill. In other embodiments, the nucleic acids are made recombinantly according to standard techniques, described, e.g., in Berger, Sambrook and Ausubel, supra.

Topoisomerase enzymes typically need only small nucleic acid substrates for activity. The design of oligonucleotide substrates for utilization in assays of eukaryotic topoisomerase enzymes is guided by the nature of the target enzyme as determined empirically and/or by reference to published information (see, Wang (1996) *Ann. Rev. Biochem.* 65:635–692 and references cited therein).

For many applications, random nucleotide sequences are suitable for use as substrates in the topoisomerase assays of the invention. In certain embodiments, however, it is desirable to include within the substrate oligonucleotide a sequence that is preferred for binding of a topoisomerase of interest. For example, substrates bearing preferred binding sites for the bacterial topoisomerase II enzyme (DNA gyrase) can be designed to incorporate the high affinity binding and cleavage sites identified, for example, in the *E. coli* chromosome (Franco et al. (1988) *J. Mol. Biol.* 201: 229–233; Condemmie et al. (1990) *Nucleic Acids Res.* 18: 7389–7397), bacteriophage Mu (Pato et al. (1990) *Proc. Natl. Acad. Sci. USA* 87: 8716–8720), or plasmids pSC101 (Miller et al. (1990) *Cell* 62: 127–133) or pBR322 (Fisher et al. (1981) *Proc. Natl. Acad. Sci. USA* 78: 4165; Morrison et al. (1981) *Proc. Natl. Acad. Sci. USA* 78:1981; Kirkegaard et al. (1981) Cell 23: 721; Lockshon et al. (1985) *J Mol. Biol.* 181: 63; O'Connor et al. (1985) *J. Mol. Biol.* 181: 545). Similarly, as will be appreciated by those skilled in the art, the design of oligonucleotide substrates for other nucleic acid topoisomerases can be designed by reference to empirically obtained or published data on experiments relating to the characterization of the sequence preferences for the target enzyme in nucleic acid binding and cleavage.

Short oligonucleotides (as opposed to longer nucleic acids) are preferred substrates for the topoisomerase assays because they can be made synthetically, because hybridization and washing in the assays leads to lower background levels and because they can be synthesized directly on the solid phase, if desired.

The oligonucleotide substrates used in the assays typically include a tag by which the oligonucleotides can be attached to a solid support. Generally, the tag is present at one end of the oligonucleotide. The tagged substrate nucleic acid is covalently or non-covalently attached to a tag (including the case noted below in which the tag is simply a terminal nucleotide (3' or 5') on the nucleic acid). Where the topoisomerase of interest becomes attached to a 5' phosphate of one of the nucleotides in the substrate, the tag is preferably attached to the 3' end of the oligonucleotide. Conversely, the tag is preferably attached to the 5' end of a substrate oligonucleotide for a topoisomerase of interest that forms a covalent linkage to a 3' phosphate.

The tag can be any of a variety of components. In general, a molecule that binds the tag (a tag binder) is fixed to a solid support, and the tagged DNA is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders (see, SIGMA Immunochemicals 1998 Catalogue, SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature (see, SIGMA Immunochemicals 1998 Catalogue, SIGMA, St. Louis Mo.). Indeed, the antibody can be either the tag or the tag binder, or antibodies can be used as both tags and tag binders. For example, in one common configuration, the tag is a first antibody and the tag binder is a second antibody that recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook,* Academic Press New York, and Hulme (ed.) *Receptor Ligand Interactions A Practical Approach,* Rickwood and Hames (series editors) Hulme (ed.) IRL Press at Oxford Press N.Y.). Similarly, toxins and venoms, viral epitopes, hormones (e.g., opiates, steroids), intracellular receptors (e.g. those that mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Specific tag-tag binder interactions occur when the tag and tag binder bind with a KD of at least about 0.01 $\mu$M, preferably at least about 0.001 $\mu$M or better, and most typically and preferably, 0.0001 $\mu$M or better, under standard assay conditions.

Synthetic attachment of DNA or RNA nucleic acids to various appropriate tags is performed using available techniques. In one embodiment, linkers are added to the nucleic acid and attachment to the tag is performed through the linker. Common linkers include polypeptide sequences, such as poly-gly sequences of between about 5 and 200 amino acids. In some embodiments, proline residues are incorporated into the linker to prevent the formation of significant secondary structural elements by the linker. Such flexible linkers are known to persons of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivitized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield (1963) *J. Am. Chem. Soc.* 85: 2149–2154 (describing solid phase synthesis of, e.g., peptides); Geysen et al. (1987) *J. Immun. Meth.* 102: 259–274 (describing synthesis of solid phase components on pins). See, Frank and Doring (1988) *Tetrahedron* 44:

6031–6040 (describing synthesis of various peptide sequences on cellulose disks); Fodor et al. (1991) *Science*, 251: 767–777; Sheldon et al. (1993) *Clinical Chemistry* 39(4): 718–719 and Kozal et al. (1996) *Nature Medicine* 2(7): 753–759 (all describing arrays of biopolymers fixed to solid substrates). Non-chemical approaches for fixing tag binders to substrates include other common methods, such as heat, cross-linking by UV radiation, and the like.

Similarly, the tagged nucleic acid may be directly attached to a solid substrate in the assays of the invention. In this embodiment, the terminal end of the tagged nucleic acid is, itself, the molecular tag. In this embodiment, tagged nucleic acids are fixed to or synthesized on a solid support. A solid support is a matrix of material in a substantially fixed arrangement. Exemplar solid supports include glasses, plastics, polymers, metals, metalloids, ceramics, organics, etc. For example, using chip masking technologies and photoprotective chemistry it is possible to generate arrays of nucleic acid probes. These arrays, which are known, e.g., as "tDNA chips," can include millions of nucleic acid regions on a substrate having an area of about 1 cm$^2$ to several cm$^2$, thereby incorporating sets of from a few to millions of tagged nucleic acids. See, e.g., Fodor et al. (1991) *Science*, 251: 767–777; Sheldon et al. (1993) *Clinical Chemistry* 39(4): 718–719, and Kozal et al. (1996) *Nature Medicine* 2(7): 753–759.

Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.).

Religation can be induced by addition of excess religation strands, in the range of 5–100× the amount of the substrate oligonucleotide, preferably 20–60×, and more preferably 40–60×.

The presence of a topoisomerase modulator in the reaction mixture will prevent or enhance complex formation between the substrate oligonucleotide and the religation strand. For example, a topoisomerase inhibitor in the reaction mixture prevents the substrate oligonucleotide from being ligated to the religation strand. Only if the proposed modulator is inactive as an inhibitor will a substrate oligonucleotide-religation strand complex be formed in the topoisomerase reaction. The tag thus functions to immobilize any oligonucleotide-religation strand complex to a solid support. The immobilization of the oligonucleotide substrate can occur either prior to, simultaneously with, or after the addition of the modulator to the reaction mixture. Alternatively, an enhancer of topoisomerase activity will increase complex formation, i.e., religation.

Topoisomerase enzymes typically need only small nucleic acid religation strands for detection of religation. Generally, the religation strand for topoisomerases are about 50 nucleotides or less in length. A preferred range for religation strands is between about 5 and about 50 nucleotides, and most preferably the substrates are between about 10 and about 25 nucleotides in length. The lower and upper size limits for religation strands employed in the present invention is often dependent upon the particular topoisomerase.

The design of oligonucleotide substrates for utilization in assays of eukaryotic topoisomerase enzymes is guided by the nature of the target enzyme as determined empirically and/or by reference to published information (see, Wang (1996) *Ann. Rev. Biochem.* 65:635–692 and references cited therein).

Short oligonucleotides (as opposed to longer nucleic acids) are preferred religation strands for the topoisomerase assays because they can be made synthetically, because hybridization and washing in the assays leads to lower background levels and because they can be synthesized directly on the solid phase, if desired.

Once the tagged nucleic acids and, if present, substrate oligonucleotide-religation strand complexes are fixed to the solid support, the support is washed to remove non-immobilized components. Wash conditions are selected so that tags remain bound to any tag binders. Preferably, a high salt wash is used, e.g., about 0.2 to 2 M NaCl or KCl. Suitable wash solutions include, for example, TBS-T buffer containing 1 M NaCl. One or more washes can be employed. In preferred embodiments, washes are repeated until at least about 50–90% of the unattached religation strand is removed from the solid support, and often until at least 90–95% is removed. The determination of how much religation strand remains can be done by performing a calibration of the assay, by performing the topoisomerase assay in the absence of a modulator and then repeatedly washing the solid support to determine the amount bound to the support through the tag, and the number of washes required to remove unbound religation strand.

The support can then be assayed to detect for religation of the substrate nucleic acid and the religation strand. The religation strand will preferably comprise a second tag that can be directly detected for or indirectly. For example, a tag selected from those discussed above as being suitable for attachment to the tagged substrate nucleic acid can be attached to the religation strand. Preferably, the tag attached to the religation strand will be different than that attached to the tagged substrate nucleic acid, so that the religation strand tag does not bind to the tag binder associated with the solid support. When a Type II topoisomerase is being used in the assays, the religation strand is double-stranded and becomes ligated to the tagged substrate nucleic acid.

Appropriate tagged religation strands, and methods for attaching the tags to polynucleotides, are known to those of skill in the art. For example, a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In *Genetic Engineering: Principles and Methods*, J. K. Setlow, Ed., Plenum Press, N.Y.; commercially available from Qiagen (Santa Clara, Calif.)).

The tags used in the assays of invention can be primary tags (where the tag comprises an element that is detected directly) or secondary tags (where the detected tag binds to a primary tag, e.g., as is common in immunological labeling). An introduction to tags (also called "labels"), tagging or labeling procedures, and detection of tags is found in Polak and Van Noorden (1997) *Introduction to Immunocytochemistry*, second edition, Springer Verlag, N.Y. and in Haugland (1996) *Handbook of Fluorescent Probes and Research Chemicals*, a combined handbook and catalogue Published by Molecular Probes, Inc., Eugene, Oreg.

Primary and secondary tags can include undetected elements as well as detected elements. Useful primary and secondary tags in the present invention can include spectral tags such as fluorescent dyes (e.g., fluorescein and derivatives such as fluorescein isothiocyanate (FITC) and Oregon Green™, rhodamine and derivatives (e.g., Texas red, tetramethyl-rhodamine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P), enzymes (e.g., horse-radish peroxidase, alkaline phosphatase) spectral calorimetric tags such as colloidal gold or colored glass or plastic (e.g. polystyrene, polypropylene, latex) beads. The tag may be coupled directly or indirectly to a component of the detection assay (e.g., the tagged nucleic acid) according to methods well known in the art. As indicated above, a wide variety of tags may be used, with the choice of tag depending on sensitivity required, ease of conjugation with the compound, stability requirements, available instrumentation, and disposal provisions. In general, a detector that monitors a probe-substrate nucleic acid hybridization is adapted to the particular tag that is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound tagged nucleic acids is digitized for subsequent computer analysis.

Preferred tags include those that utilize 1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; 2) color production (using both Horseradish Peroxidase and/or Alkaline Phosphatase with substrates that produce a colored precipitate) (kits available from Life Technologies/Gibco BRL, and Boehringer-Mannheim); 3) hemifluorescence using, e.g., Alkaline Phosphatase and the substrate AttoPhos (Amersham) or other substrates that produce fluorescent products, 4) Fluorescence (e.g., using Cy-5 (Amersham), fluorescein, and other fluorescent tags); 5) radioactivity using kinase enzymes or other end-labeling approaches, nick translation, random priming, or PCR to incorporate radioactive molecules into the tagged nucleic acid. Other methods for tagging and detection will be readily apparent to one skilled in the art.

Fluorescent tags are highly preferred tags, having the advantage of requiring fewer precautions in handling, and being amendable to high-throughput visualization techniques (optical analysis including digitization of the image for analysis in an integrated system comprising a computer). Preferred tags are typically characterized by one or more of the following: high sensitivity, high stability, low background, low environmental sensitivity and high specificity in tagging. Fluorescent moieties, which are incorporated into the tags of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA Chemical Company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie AG, Buchs, Switzerland), and Applied Biosystems (Foster City, Calif.), as well as many other commercial sources known to one of skill.

Most typically, topoisomerase inhibition is measured by quantifying the amount of tag fixed to the solid support by the capture of the covalently linked complex between oligonucleotide and topoisomerase that occurs in the presence of an agent that inhibits topoisomerase activity. Typically, the presence in the reaction mixture of a modulator that modulates (enhances or inhibits) topoisomerase activity will increase or decrease, respectively, the amount of tag fixed to the solid support relative to a control reaction that does not comprise the modulator, or as compared to a baseline established for a particular lot of topoisomerase. Means of detecting and quantifying tags are well known to those of skill in the art. Thus, for example, where the tag is a radioactive tag, means for detection include a scintillation counter or photographic film as in autoradiography. Where the tag is optically detectable, typical detectors include microscopes, cameras, phototubes and photodiodes and many other detection systems that are widely available.

Model Solid Phase Oligonucleotide-based Assays

The solid phase oligonucleotide-based assays of the invention are further illustrated by the following. These assays are provided by way of illustration and not by way of limitation; one of skill will recognize a variety of substitutions that can be made upon complete review of this disclosure.

A substrate DNA having a biotin tag attached to its 5' end is placed in a reaction solution with a Type I topoisomerase (complexed with substrate nucleic acid or independent), a single-stranded tagged religation strand and a topoisomerase modulator. Alternatively, If the modulator inhibits the enzymatic function of the topoisomerase, then the tagged religation strand cannot be ligated to the substrate DNA. The solution is placed in a streptavidin or neutravidin coated plate, and, if present, the substrate DNA-religation strand complex will attach to the plate by means of the biotin tag. The presence of a topoisomerase inhibitor in the reaction mixture results in preventing the substrate DNA-religation strand complex from forming. A labeled antibody that binds to the tag of the religation strand is then placed in contact with the solid support. The amount of enzyme activity is measured by chemiluminescence, preferably after washing to remove any unbound antibody from the solid support. The intensity of the chemiluminescesnce is inversely proportional to the effectiveness of the topoisomerase inhibitor.

In a second embodiment, the conditions are the same as above, except a Type II topoisomerase is used, and the tagged religation strand is double-stranded.

Liquid Phase Assays

The liquid phase assays of the invention provide methods of measuring the activity of topoisomerase in the presence of a potential topoisomerase activity modulator. In the methods, a test reaction mixture including a topoisomerase, a substrate nucleic acid and a religation strand is incubated in a liquid phase. Typically, the substrate nucleic acid has a first tag and the religation strand has a second tag. Most typically in the liquid phase assays of the invention, the first and second tag interact when in proximity (e.g., due to resonance transfer), and the relative proximity of the first and second tags is determined by measuring a change in the intrinsic fluorescence of the first or second tag. Commonly, the emission of the first tag is quenched by proximity of the second tag. After incubation, the presence or absence of a detectable tag emission is detected. The detected emission can be any of the following: an emission by the first tag, an emission by the second tag, and an emission resulting from a combination of the first and second tag. Typically, a change in the signal, due to religation inhibition of the substrate nucleotide to the religation strand by the inhibitor, is detected (e.g., a reduction in quenching that leads to an increase in signal from either or both of the tags, a change in signal color, and the like).

Many appropriate interactive tags are known. For example, fluorescent tags, dyes, enzymatic tags, and antibody tags are all appropriate. Examples of preferred interactive fluorescent tag pairs include terbium chelate and TRITC (tetramethylrhodamine isothiocyanate), europium cryptate and Allophycocyanin and many others known to one of skill. Similarly, two colorimetric tags can result in combinations that yield a third color, e.g., a blue emission in proximity to a yellow emission provides an observed green emission.

With regard to preferred fluorescent pairs, there are a number of fluorophores that are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of tags occurs. Fluorescent resonance energy transfer (FRET) is a distance dependent excited state interaction in which emission of one fluorophore is coupled to the excitation of another that is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals,* Published by Molecular Probes, Inc., Eugene, Oreg., e.g., at chapter 13).

An extensive compilation of RP values are found in the literature; see, Haugland (1996) *Handbook of Fluorescent Probes and Research Chemicals* Published by Molecular Probes, Inc., Eugene, Oreg. at page 46 and the references cited therein.

In most uses, the first and second tags are different, in which case FRET can be detected by the appearance of sensitized fluorescence of the acceptor or by quenching of the donor fluorescence. When the first and second tags are the same, FRET is detected by the resulting fluorescence depolarization.

In addition to quenching between fluorophores, individual fluorophores are also quenched by nitroxide-tagged molecules such as fatty acids. Spin tags such as nitroxides are also useful in the liquid phase assays of the invention.

In the liquid phase methods of the invention, a substrate nucleic acid species having one tag is contacted with a religation strand having a second tag in the presence of a topoisomerase and a potential topoisomerase activity modulator. The first and second tags are spaced such that, upon religation of the substrate nucleic acid and the religation strand, both two tags are present on the same molecule of nucleic acid, and therefore, the signal resulting from the tags changes. This can be easily determined empirically for any combination of tag pairs. Typically, the first and second tags will be between about 8 and about 40 nucleotides apart.

The liquid phase assays of the invention are performed in essentially any liquid phase containers designed for high throughput screening. Most commonly, the religation mixture is incubated in a well on a microtiter dish (many dish formats are known, e.g., 96 well, 384 well, etc).

Compositions, Kits and Integrated Systems

The invention provides compositions, kits and integrated systems for practicing the assays described herein. For example, an assay composition having a topoisomerase enzyme, a substrate nucleic acid molecule comprising a first tag, a religation strand comprising a second tag, a topoisomerase activity modulator and a tagged moiety is provided by the present invention. Typically, in the solid phase assays, the tag binds to a tag-binding molecule fixed to a solid substrate, thereby immobilizing the tagged nucleic acid on the solid substrate. Example tags include biotin, antibodies and the like as discussed above.

Similarly, a liquid phase assay composition includes a topoisomerase enzyme, a substrate nucleic acid molecule comprising a first tag, a religation strand comprising a second tag, and a topoisomerase activity modulator. As discussed in detail above, the first tag is typically quenched by the second tag (or the second quenched by the first) when the first and second tags are in close proximity. In the example noted above, the first tag is quenched by the second tag when the first tag is within about 10 nm of the second tag. Thus, when a topoisomerase becomes inhibited by the modulation, resulting in no religation of the substrate nucleic acid to the religation strand, there is no quenching.

The invention also provides kits for practicing the methods noted above. The kits can include any of the compositions noted above, and optionally further include additional components such as instructions to practice a high-throughput method of screening for a topoisomerase inhibitor, one or more containers or compartments (e.g., to hold topoisomerase enzyme, nucleic acids, or the like), a control topoisomerase activity modulator, a robotic armature for mixing kit components or the like.

The invention also provides integrated systems for high-throughput screening of potential topoisomerase modulators for an effect on a topoisomerase. The systems typically include a robotic armature that transfers fluid from a source to a destination, a controller that controls the robotic armature, a tag detector, a data storage unit that records tag detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous topoisomerase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intelx86 or Pentium chip-compatible DOS™, OS2™ WINDOWS™, WINDOWS NT™ or WINDOWS95™ based computers), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Compounds Useful in the Present Invention

The present invention provides methods of screening or identifying proteins, small molecules or other compounds that are capable of inhibiting topoisomerase religation activity. The assays are performed in vitro. In particular, the assays may detect the inhibition of topoisomerase religation activity on the basis of an increased or decreased level of a tag (e.g., digoxigenin). The test DNA is incubated in the presence of one or more test compounds. After allowing a sufficient period of time (e.g., 0–72 hours) for the compound to inhibit the topoisomerase religation activity, any change in levels of the tag from an established baseline is detected using any known technique, such as by ELISA.

The present invention provides methods for identifying proteins and other small molecule compounds that bind to, or otherwise directly interact with, the topoisomerase religation activity. The proteins and compounds will include endogenous cellular components that interact with the topoisomerase in vivo that provide new targets for pharmaceutical and therapeutic interventions. They can be employed for a variety of conditions, including antibacterial, antifungal, antiviral or anti-neoplastic agents. The proteins and compounds also include recombinant, synthetic and otherwise exogenous compounds that have topoisomerase IB binding capacity and, therefore, are candidates for pharmaceutical agents. Thus, any of a variety of exogenous compounds, both naturally occurring and/or synthetic (e.g., libraries of small molecules or peptides), may be screened for topoisomerase ligation modulation (inhibition or activation) capacity.

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

A variety of other compounds may be included in the method of the present invention. These include agents like salts, neutral proteins, e.g., albumin, detergents, etc. that are used to facilitate optimal protein-protein binding or interactions and/or reduce nonspecific or background binding or interactions. For example, reagents that improve the efficiency of the assay, such as protease inhibitors, nuclease inhibitors, antimicrobial agents, may be used. The mixture of components are added in any order that provides for the requisite modulation. Moreover, such compounds additionally can be modified so as to facilitate their identification or purification. Such modifications are well known to the skilled artisan (e.g., biotin and streptavidin conjugated compounds).

In another series of embodiments, the present invention provides methods and pharmaceutical preparations for use in the treatment of topoisomerase IB-associated diseases such as pathogenic infections and cancer. These methods and pharmaceuticals are based upon administration of small molecules (drugs) that are modulators of topoisomerase.

1. Formulations of Compounds

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts.

Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

The compounds may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Assays of other DNA modifying enzymes

Alternative variations of the above-described assays can be used to detect the activity of several other DNA modifying enzymes. Such assays could be used to screen for candidate inhibitors. In each case the assays rely on using DNA modifying enzymes to covalently attach a detection tag to an affinity capture tag. Such assays comprise steps similar to the topoisomerase assay, i.e., capture of product on a solid support, washing, and detection of the detection tag. Additional applications are listed below.

1. Detection of ligase activity. In this embodiment, two double stranded DNAs are used. One double stranded DNA contains the affinity capture tag, the second contains the detection tag. The DNA 5' ends on the opposite ends of the DNA chain from the tags contain 5' phosphates. Action of ligase connects the two covalently. The product is then captured on a solid support and the detection tag assayed.

2. Detection of ligase cofactors. Several cofactors have been described that promote ligase activity. For human ligases, XRCC1 stimulates ligase III, and XRCC4 stimulates ligase IV. Ku protein stimulates DNA end joining by ligase IV by opposing DNA ends. The above assay could be adapted so as to make the ligation reaction dependent on the added cofactor. One simple way would be by the addition of sub-optimal amounts of ligase enzyme. The stimulatory effect of the cofactor could then by detected by the ligase assay described above. Inhibitors of the cofactor could then be detected by screening of candidate small molecules.

3. Detection of DNA kinase activity. This assay is carried out as above, but the reactant DNAs are not phophorylated on the DNA 5' ends. This prevents ligase from connecting the DNA molecules. Addition of an appropriate DNA kinase and ATP allows the DNA ends to be phosphorylated, which permits subsequent ligation. The DNA products are then captured and assayed as above.

4. Detection of polymerase activity. Many polymerases will incorporate modified dNTP or rNTP bases, allowing the assay of polymerase activity by the described method. In this embodiment, one tag would be attached to the polymerization template, the other to the nucleotide to be added to the growing chain. Polymerization results in the covalent attachment of one tag to the other. Inhibitors can then be identified by addition of candidate small molecules to such reactions. The method can be adapted to assay DNA polymerases, RNA polymerases, or reverse transcriptases.

5. Detection of DNAse activity. DNAse enzymes cleave DNA molecules. Such activities could be detected using a DNA substrate with a capture tag on one end and a detection tag on the other. DNAse activity would result in cleavage of the DNA molecule, thereby separating the two tags. Enzyme activity would be detected as a reduction in detection of the detection tag.

6. Detection of RNAse activity. RNAse enzymes cleave RNA molecules. Such activities could be detected as above, but using an RNA substrate with an affinity tag on one end and a detection tag on the other.

7. Detection of RNAseH activity. RNAseH enzymes act by cleaving the RNA component of RNA-DNA hybrids. In this embodiment, the RNA would contain the capture tag on one end and the detection tag on the other end at the start of the assay. RNAseH activity would result in the separation of the two tags, allowing detection of activity as a reduction in capture of the detection tag.

For all of the above assays, uses include but are not restricted to identification of inhibitors of 1) human enzymes for use as anticancer agents and, 2) pathogen enzymes for use as antimicrobial agents.

The following examples are intended to illustrate but not limit the invention.

EXAMPLES

Rapid microtiter assays for function of topoisomerases and their use in identifying selective modulatory small molecules have been developed by the inventors. Model oligonucleotide DNAs are modified so that the topoisomerase religation activity forms a strand containing a first tag, such as a biotin group on one end and a second tag, such as a digoxigenin group, on the other. This allows the reaction to be quantitated by capturing biotinylated product DNA on avidin-coated plates followed by detection using an anti-digoxigenin ELISA. The order of addition of reactants and inhibitors can be varied to distinguish effects of test compounds on different steps in the topoisomerase reaction. This highly efficient assay was used to screen compound libraries for inhibitors active against mammalian or pox virus type IB topoisomerases.

The present rapid microtiter assay allows discrimination of effects at different reaction steps and in the presence of different sequences at the point of DNA incision. The method allows much more efficient characterization of topoisomerase function and topoisomerase inhibition.

The microtiter assay screen was used to identify a compound (−)-epigallocatechin 3-O-gallate (EGCG), a natural product from green tea, that inhibited EU-TOPO with an IC 50 of 26 nM. EGCG is far more inhibitory on the DNA substrate containing a G/C base pair 3' of the point of cleavage in the covalent intermediate rather than A/T. This supports a model in which the inhibitor makes base-specific contacts to the DNA 3' of the nick, as has been argued previously for other inhibitors (Y. Fan, J. N. Weinstein, K. W. Kohn, L. M. Shi and Y. Pommier. 1998. Molecular Modeling Studies of the DNA-Topoisomerase I Ternary Cleavable Complex with Camptothecin. *J. Med. Chem.* 41, 2216–2226; M. R. Redinbo, L. Stewart, P. Kuhn, J. J. Champoux and W. G. J. Hol. 1998. Crystal Structures of Human Topoisomerase I in Covalent and Noncovalent Complexes with DNA. *Science* 279, 1504–1513). This observation emphasizes the utility of repeated screens for topoisomerase inhibitors using different sequences around the point of cleavage.

As examples of the present invention, described below are microtiter plate assays that monitor religation by two type IB topoisomerases, EU-TOPO and that of MCV (MCV-TOP). The inventors have used the new microtiter assay to screen libraries of small molecules for inhibitory activities.

Example 1

A Microtiter Plate Assay for MCV Topoisomerase

Figure 1:
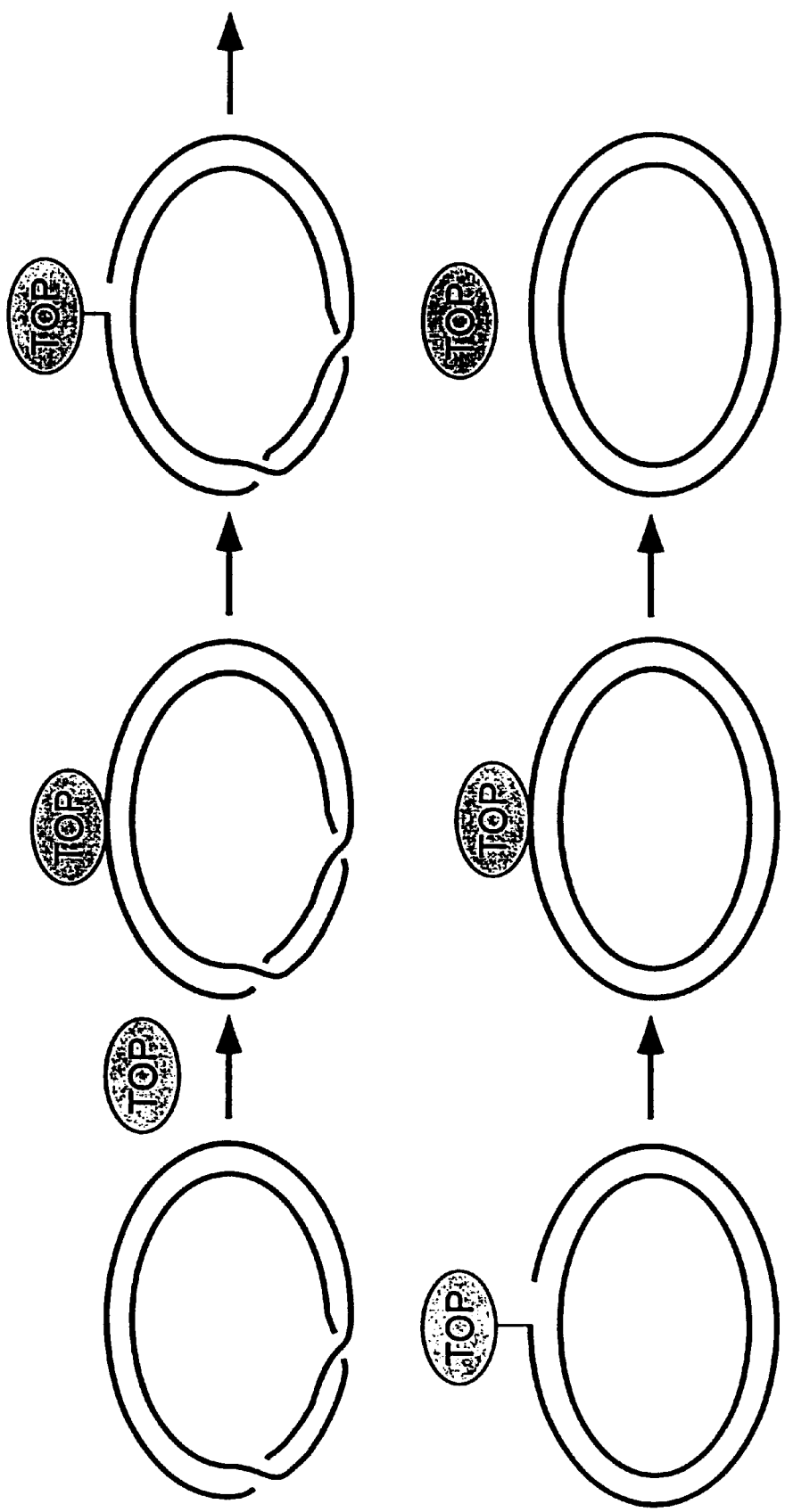
FIG. 1. Diagram of the mechanism of type IB topoisomerases. The topoisomerase is shown by the gray ball; DNA is shown by the thick lines.
Figure 2:
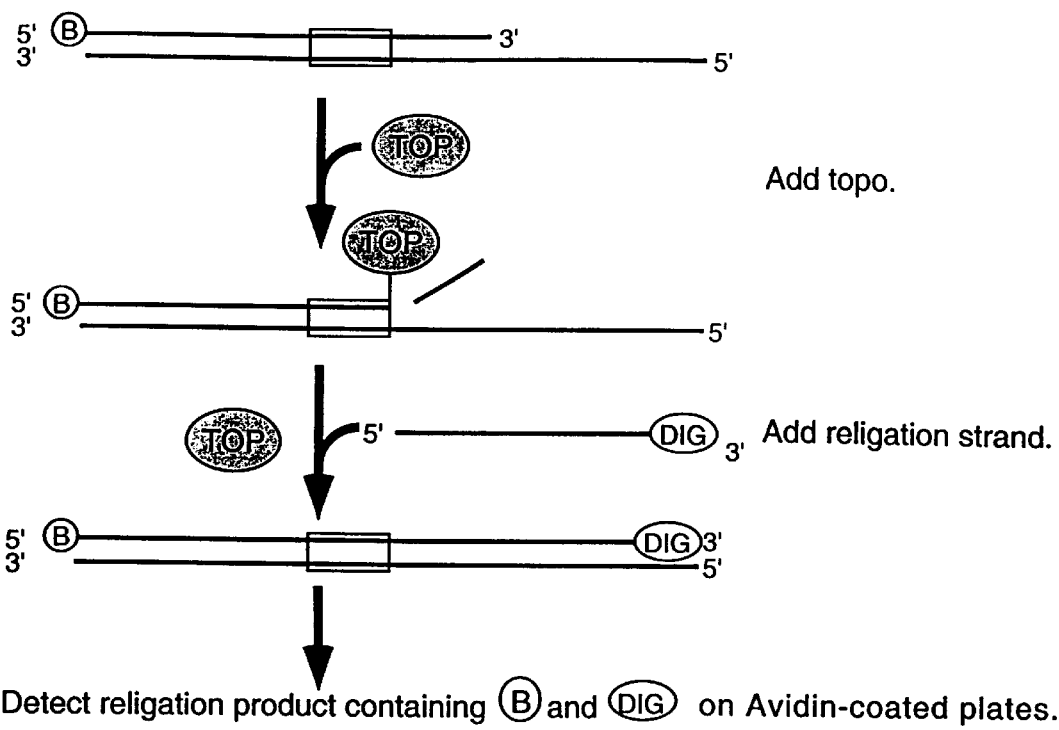
FIG. 2. Rapid microtiter assays for type IB topoisomerases. A. Strategy for using the topoisomerase religation reaction for rapid product detection. The suicide substrate containing biotin on the 5' end of the top strand (indicated by the "B") was incubated with a type IB topoisomerase (top). Formation of the covalent complex cleaves the DNA and releases the short duplex extension 3' of the cleavage site (middle), thereby trapping the covalent complex. This allows the religation reaction to be carried out by addition of a religation strand containing digoxigenin (bottom). The extent of product formation is then monitored by capturing the strand containing biotin and digoxigenin.
Figure 2:
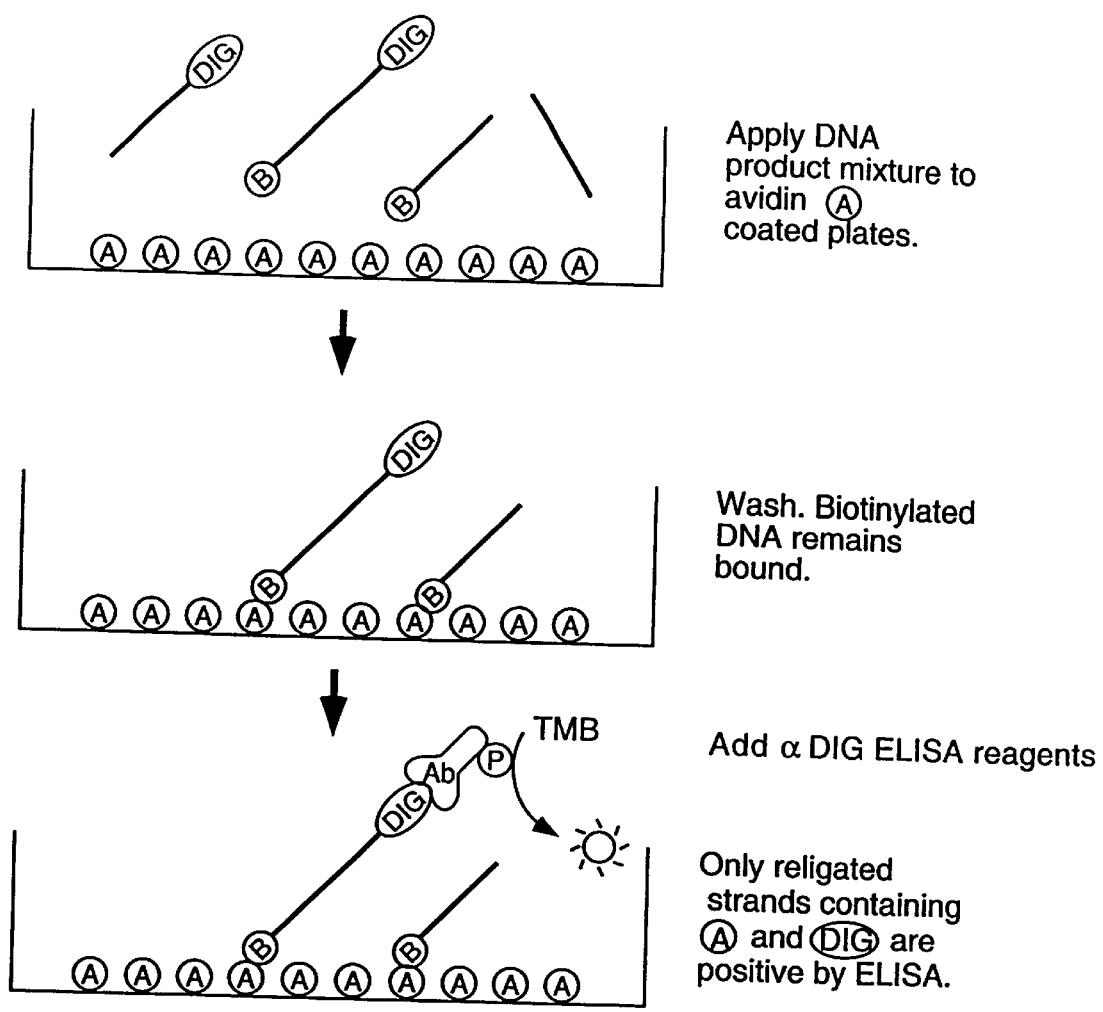

The sequence-specific binding of MCV-TOP (Y. Hwang, B. Wang and F. D. Bushman. 1998. Molluscum contagiosum virus topoisomerase: purification, activities and response to inhibitors. *J. Virol.* 72, 3401–3406; Y. Hwang, A. Burgin and F. D. Bushman. 1999. DNA Contacts Stimulate Catalysis by a Poxvirus Topoisomerase. *J. Biol. Chem.* 274, 9160–9168) was exploited to position a topoisomerase binding site near the end of a short duplex oligonucleotide (MCV sub a', FIG. 2B). Formation of the covalent complex cleaves the top strand of MCV sub a' (strand HW375; FIG. 2A, top). The 5 base strand 3' of the resulting DNA nick is too short to remain annealed, and so dissociates and is lost by dilution. This traps the covalent complex (FIG. 2A, middle). Such substrates have been called "suicide substrates" in previous literature (E. Richet, P. Abcarian and H. A. Nash. 1988. Synapsis of Attachment Sites during Lambda Integrative Recombination Involves Capture of a Naked DNA by a Protein-DNA Complex. *Cell* 52, 9–17; A. B. J. Burgin, B. N. Huizenga and H. A. Nash. 1995. A novel suicide substrate for DNA topoisomerases and site-specific recombinases.

*Nuc. Acids Res.* 23, 2973–2979; S. Shuman. 1992. DNA Strand Transfer Reactions Catalyzed by Vaccinia Topoisomerase I. *J. Biol. Chem.* 267, 8620–8627). Addition of a new DNA strand (HW378) complementary to the single stranded region in the suicide substrate allows attack of the 5' hydroxyl of the added strand at the topoisomerase-DNA phosphotyrosine linkage. This joins the newly added "religation strand" (HW378) to the starting top strand (HW375; FIG. 2A, bottom).

To permit detection of the religation product, a biotin group is attached to the 5' end of the cleavable strand (HW375), and a digoxigenin group is attached to the 3' end of the religation strand (HW378). Thus the religation reaction generates a DNA strand that has biotin on one end and digoxigenin on the other. This DNA strand is then captured by applying the reaction products to an avidin coated plate (FIG. 2C). After washing, the amount of product is detected by addition of an anti-digoxigenin Fab linked to peroxidase, followed by washing and addition of a colorometric substrate. The colored product formed by the peroxidase reaction is then quantitated by spectrophotometry. Each step in the process is carried out in 96-well plates, greatly speeding throughput compared to earlier gel-based assays.

Test reactions carried out under a variety of conditions are presented in FIG. 3. No product formation was detected in reactions lacking MCV-TOP, anti-digoxigenin peroxidase-Fab, DNA substrate MCV sub a', or TMB peroxidase substrate. In addition, no activity was detected when a DNA substrate for EU-TOPO was substituted for MCV sub a', indicating the sequence specificity of MCV-TOP.

Example 2

A Microtiter Plate Assay for EU-TOPO

The present inventors also developed a similar assay for function of EU-TOPO, a known target for anticancer drugs. The DNA substrate was designed to contain a preferred site for topoisomerase IB action identified in Tetrahymena DNA (A. H. Andersen, E. Gocke, B. J. Bonven, O. F. Nielsen and O. Westergaard. 1985. Topoisomerase I has a strong binding preference for a conserved hexadecameric sequence in the promoter region of the rRNA gene from *Tetrahymena pyriformis*. *Nuc. Acids Res.* 13, 1543–1556; B. J. Bonven, E. Bocke and O. Westergaard. 1985. A High Affinity Topoisomerase I Binding Sequence is Clustered at DNase I Hypersensitive Sites in Tetrahymena R-Chromatin. *Cell* 41, 541–551).

Initial tests using substrate EU TG (FIG. 2B) revealed relatively low activity. To investigate this, a comparison of religation activities of substrates EU TG and EU TG+P using $^{32}P$ tagged substrates and gel electrophoresis was performed. Assays were carried out with oligonucleotides matching substrate EU TG except lacking the biotin and digoxigenin modifications (strands HW406 and HW407 respectively). Oligonucleotide HW406 was 5' tagged with $^{32}P$, and annealed with HW404. Covalent complexes were formed by incubation with EU-TOPO, the further incubated after addition of the religation strand (HW407). The gel was prepared as follows: Lane 1) 30 base marker for the expected religation product, lane 2) 45 base marker matching the self-religated hairpin product, lane 3) substrate EU TG, lane 4) substrate EU TG+EU-TOPO, lane 5) substrate EU TG+EU-TOPO+religation strand, lane 6) substrate EU TG+P only (see sequence HW 410, FIG. 2B), lane 7) substrate EU TG+P+EU-TOPO, lane 8) substrate EU TG+P+EU-TOPO+religation strand. The sequences of the markers were 5' GATCGAAAAAGACTTGGAAAAATTATCGGC 3' (lane 1; HW408, the expected religation product) and 5' GATCGAAAAAGACTTGCCGATAATTTTTCCAAGTCTTTTTCGATC 3' (lane 2; HW412, the self-religated hairpin product).

Tagged DNA products were visualized by electrophoresis and autoradiography. DNA oligonucleotides matching expected reaction products were synthesized, tagged, and subjected to electrophoresis in adjacent lanes. These assays revealed much less formation of the religated DNA strand than in comparable assays with MCV-TOP (for MCV-TOP see (Y. Hwang, D. Rowley, D. Rhodes, J. Gertsch, W. Fenical and F. D. Bushman. 1999. Mechanism of inhibition of a poxvirus topoisomerase by the marine natural product sansalvamide A. *Mol. Pharmacol.* 55, 1049–1053; Y. Hwang, M. Park, W. H. Fischer and F. Bushman. 1999. Domain structure of the type-1B topoisomerase encoded by molluscum contagiosum virus. *Virology* 262, 479–491)).

Figure 4A:
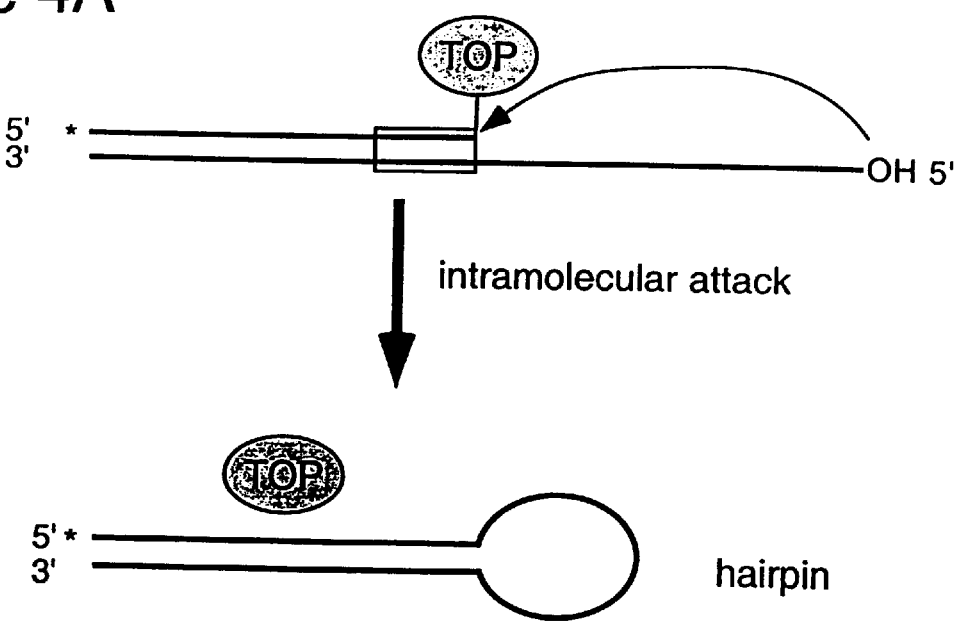

However, an unexpected DNA form was produced in abundance. These products migrated with a DNA marker (HW412) matching that expected from joining the 5' end of strand HW404 at the covalent phosphotyrosine bond. This product was probably formed by an intramolecular reaction in which the single stranded 5' end region of oligonucleotide HW404 attacks a EU-TOPO covalent complex, forming a hairpin (FIG. 4A). Alternatively, this could have been formed by a second copy of strand HW404 attacking the covalent intermediate on another DNA duplex. Intramolecular hairpin formation has been reported previously for phage lambda integrase, a related enzyme (E. Richet, P. Abcarian and H. A. Nash. 1988. Synapsis of Attachment Sites during Lambda Integrative Recombination Involves Capture of a Naked DNA by a Protein-DNA Complex. *Cell* 52, 9–17). To reduce formation of this side product, the reactive 5' OH end of oligonucleotide HW404 was blocked by phosphorylation (FIG. 2B, EU TG+P, strands HW410 and HW413). This resulted in reduced formation of the "self-religated" product and much greater production of the desired religation strand. In the plate assay this resulted in a four-to-six-fold increase in product formation. Phosphorylation did not block hairpin formation completely, however, due to incomplete phosphorylation of the strand HW410 during chemical synthesis. Why EU-TOPO but not MCV-TOP favored hairpin formation is unclear, but is of interest for possible insight into the reaction mechanism.

Figure 4B:
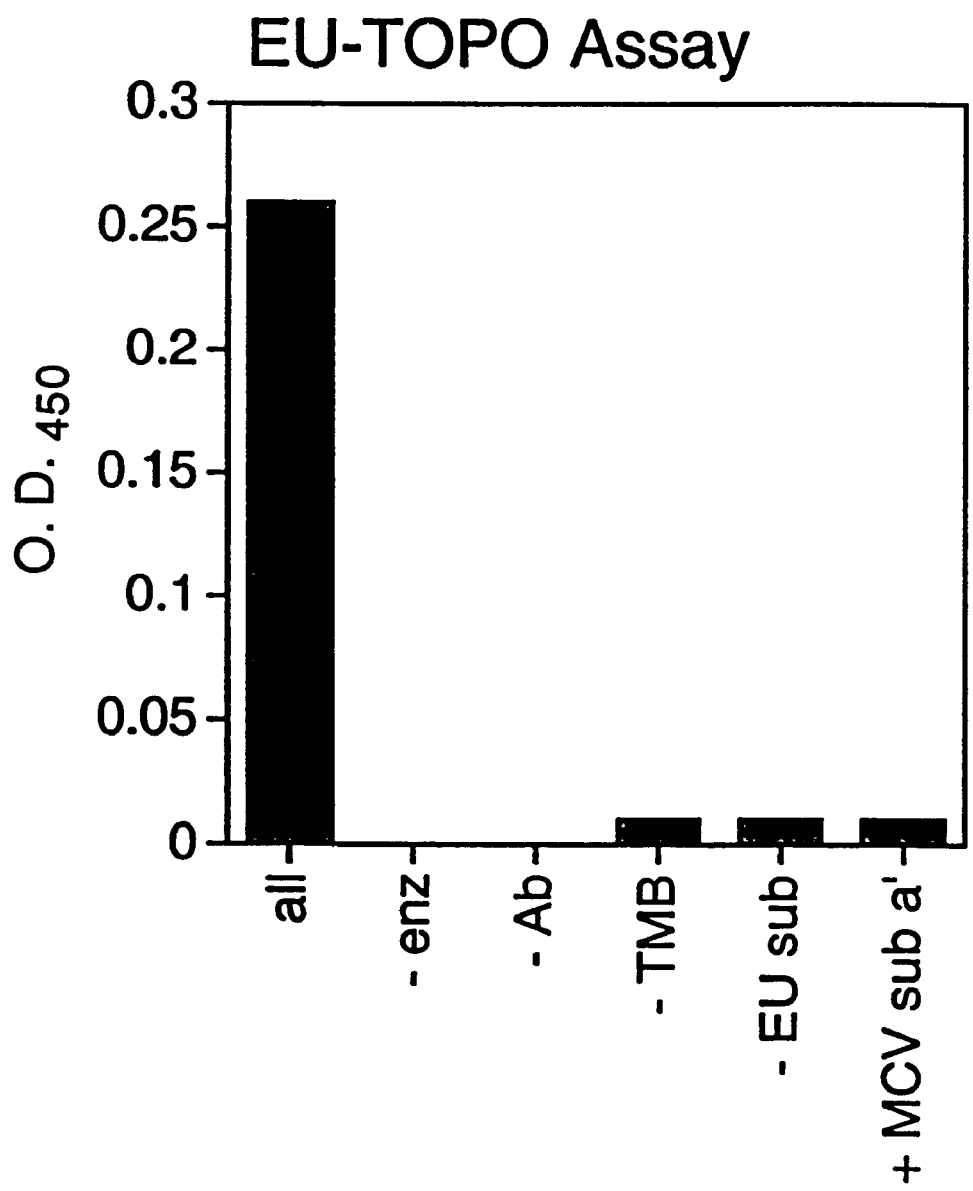

Characterization of the requirements for product formation for the EU-TOPO reaction is shown in FIG. 4B. No activity was detected when EU-TOPO, anti-digoxigenin-peroxidase Fab fragment, TMB, or EU TG+P substrate DNA was omitted from the reaction (FIG. 4B). In addition, no activity was detected when oligonucleotide MCV sub a' was substituted for EU TG+P, documenting the sequence specificity of EU-TOPO (FIG. 4B).

Example 3

Response of the Microtiter Assay to Known Topoisomerase Inhibitors

As a first step in applying this assay to inhibitor identification, the effect of known topoisomerase inhibitors was tested (FIG. 5). Two orders of addition were compared. Reactions were carried out in which enzyme was preincubated with inhibitor before addition of DNA substrate (FIG. 5, "complete"), which would reveal inhibition at any step in the reaction pathway. Reactions were also carried out in which covalent complexes were formed, then inhibitor added, followed by the religation strand (FIG. 5, "religation"). The latter order of addition tested inhibition of the religation step only.

For EU-TOPO, two different substrate DNAs were tested, containing TA or TG as the bases flanking the scissile phosphate. It has been suggested that some EU-TOPO religation inhibitors form a ternary complex involving contacts to the base 3' of the point of incision (C. Jaxel, G. Capranico, D. Kerrigan, K. W. Kohn and Y. Pommier. 1991. Effect of Local DNA Sequence on Topoisomerase I Cleavage in the Presence or Absence of Camptothecin. *J. Biol. Chem.* 266, 20418–20423; A. Tanizawa, K. W. Kohn and Y. Pommier. 1993. Induction of cleavage in topoisomerase I c-DNA by topoisomerase I enzymes from calf thymus and wheat germ in the presence and absence of camptothecin. *Nuc. Acids Res.* 21, 5157–5166; Y. Fan, J. N. Weinstein, K. W. Kohn, L. M. Shi and Y. Pommier. 1998. Molecular Modeling Studies of the DNA-Topoisomerase I Ternary Cleavable Complex with Camptothecin. *J. Med. Chem.* 41, 2216–2226), so such effects were sought to be discriminated using the microtiter assay.

Coumermycin A1 (Sigma Chemicals, St. Louis, Mo.), a known MCV-TOP inhibitor was tested and found to inhibit the complete reaction, but not religation by MCV-TOP (FIG. 5A). Camptothecin (Sigma Chemicals, St. Louis, Mo.), an inhibitor of EU-TOPO, was not active against MCV-TOP.

Coumermycin A1 also inhibited EU-TOPO. In this case inhibition of the complete reaction and religation was comparable. Evidently for EU-TOPO coumermycin is capable of acting on the covalent intermediate. Inhibition by coumermycin was not sensitive to the identity of the base 3' of the scissile phosphate (compare FIGS. 5B and 5C). Inhibition of EU-TOPO by camptothecin, in contrast, was more efficient when the 3' base was G, as expected from previous reports (Y. Fan, J. N. Weinstein, K. W. Kohn, L. M. Shi and Y. Pommier. 1998. Molecular Modeling Studies of the DNA-Topoisomerase I Ternary Cleavable Complex with Camptothecin. *J. Med. Chem.* 41, 2216–2226; M. R. Redinbo, L. Stewart, P. Kuhn, J. J. Champoux and W. G. J. Hol. 1998. Crystal Structures of Human Topoisomerase I in Covalent and Noncovalent Complexes with DNA. *Science* 279, 1504–1513) (FIGS. 5B and 5C).

Example 4

Screening for Inhibitors of Topoisomerases

The microtiter assays for MCV-TOP and EU-TOPO were next used to screen libraries of pure compounds and natural product extracts. Several fractions with inhibitory activity were identified and are under study (unpublished data).

The most potent inhibitor of EU-TOPO identified was (−)-epigallocatechin 3-O-gallate (EGCG) (Sigma Chemicals, St. Louis, Mo.), a natural product from green tea (FIG. 6A). EGCG inhibited religation by EU-TOPO with an IC50 of 26 nM for the EU TG+P substrate. On the EU TA+P substrate, however, the IC50 was 500 nM, indicating selectivity for the base 3' of the scissile phosphate (FIG. 6B). EGCG had no effect on MCV-TOP in this concentration range. EGCG has been reported to have anticancer properties based on previous studies in vivo (19–21). The present data suggest that EGCG may exert its anticancer effects at least in part by inhibiting religation by EU-TOPO.

Example 5

Topoisomerase Activity Assays

MCV-TOP was purified using nickel-chelating sepharose as described (Y. Hwang, B. Wang and F. D. Bushman. 1998. Molluscum contagiosum virus topoisomerase: purification, activities and response to inhibitors. *J. Virol.* 72, 3401–3406). Standard reaction mixtures for assaying MCV-TOP contained 10 nM MCV-TOP, 2 nM substrate oligonucleotide, 20 mM Tris-Cl (pH 8.0), 200 mM potassium glutamate, 1 mM DTT, 0.1% Triton X-100 and 10% DMSO. The MCV-TOP substrate used for this assay was derived from a previously characterized optimal sequence (sub a) (Y. Hwang, B. Wang and F. D. Bushman. 1998. Molluscum contagiosum virus topoisomerase: purification, activities and response to inhibitors. *J. Virol.* 72, 3401–3406). In the version of the substrate used here (MCV sub a', see FIG. 2B), the 5 base duplex extension 3' of the 5'-CCCTT-3' sequence can dissociate upon covalent complex formation. This traps the covalent complex but permits religation to an added complementary DNA strand. Following covalent complex formation, religation was initiated by addition of 2-fold excess of a tagged 15-mer single strand DNA (HW378, see FIG. 2B). To test inhibition of covalent complex formation, chemicals were added to the enzyme and preincubated for 5 min and then the reaction was started with addition of oligonucleotide substrate. To test inhibition of the religation step, topoisomerase was mixed with substrate and incubated to allow covalent complex formation. Test chemicals were then added to the reaction followed by the religation substrate. All steps were carried out at 37° C.

Standard reaction mixture for assaying EU-TOPO contains 2.5 units EU-TOPO, 2 nM substrate oligonucleotide, 20 mM Tris-Cl (pH 8.0), 72 mM KCl, 5 mM MgCl2, 5 mM DTT and 10% DMSO. EU-TOPO was obtained from Gibco-BRL. The EU-TOPO suicide substrate was based on an optimal sequence found in a Tetrahymena rRNA gene (see FIG. 2B) (A. H. Andersen, E. Gocke, B. J. Bonven, O. F. Nielsen and O. Westergaard. 1985. Topoisomerase I has a strong binding preference for a conserved hexadecameric sequence in the promoter region of the rRNA gene from *Tetrahymena pyriformis. Nuc. Acids Res.* 13, 1543–1556; B. J. Bonven, E. Bocke and O. Westergaard. 1985. A High Affinity Topoisomerase I Binding Sequence is Clustered at DNase I Hypersensitive Sites in Tetrahymena R-Chromatin. *Cell* 41, 541–551).

Example 6

Gel Assay for Activity of EU TOPO

Substrate HW406 (sequence: 5' GATCGAAAAAGACT-TGGAAA 3') was tagged on the 5' end by treatment with $^{32}$PATP and kinase. Tagged HW406 was annealed with HW404 for EU TG or HW410 for EU TG+P, and 50 nM DNA was incubated with 12 units of protein in the buffer described for assays above. The formation of covalent complexes was carried out for 12 hours, and then the religation reaction was started with addition of 100 nM religation strand (HW407; sequence 5' GGAAAAATTATCGGC-3') and incubated for two hours at room temperature. The reaction products were analyzed on DNA sequencing type acrylamide gels and visualized by autoradiography.

Example 7

Detection of Topoisomerase Products in Avidin-coupled Microtiter Wells

After the topoisomerase reactions were completed, mixtures were adjusted to 20 mM Tris-Cl (pH 8.0), 400 mM NaCl, 10 mM EDTA, and 0.1 mg/ml sonicated salmon sperm DNA in a final volume of 100 µl. 400 mM NaCl was omitted in EU-TOPO assay. The samples were added to avidin-coupled microtiter wells (Boehringer Mannheim), which were then gently agitated at room temperature for 1 hr. Unbound DNA was removed by 3 washes (200 µl, 5 min each) with 30 mM NaOH, 200 mM NaCl, 1 mM EDTA. Bound DNA was then adjusted to 10 mM Tris-Cl (pH 8.0) and 1 mM EDTA. The relative topoisomerase activity was determined using an anti-digoxigenin ELISA. Anti-digoxigenin-peroxidase Fab fragments (0.01 units, Pierce or Boehringer Mannheim) were added into wells and incubated for 1 hr at 37° C. Unbound Anti-digoxigenin peroxidase Fab fragments were removed by 5 washes (300 µl) with PBS containing 0.1% Tween 20. Bound DNA was then incubated with 200 µl of 3,3'-5,5'-tetramethylbenzidine (TMB) solution (Boehringer Mannheim) until sufficient blue product accumulated. The reaction was terminated by adding 100 µl of 1 M sulfuric acid. The resulting yellow color was quantitated at 450 nm.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

REFERENCES

1. A. H. Andersen, E. Gocke, B. J. Bonven, O. F. Nielsen and O. Westergaard. 1985. Topoisomerase I has a strong binding preference for a conserved hexadecameric sequence in the promoter region of the rRNA gene from *Tetrahymena pyriformis*. *Nuc. Acids Res.* 13, 1543–1556.
2. B. J. Bonven, E. Bocke and O. Westergaard. 1985. A High Affinity Topoisomerase I Binding Sequence is Clustered at DNase I Hypersensitive Sites in Tetrahymena R-Chromatin. *Cell* 41, 541–551.
3. S. Shuman. 1998. Vaccinia virus DNA topoisomerase: a model eukaryotic type IB enzyme. *Biochim. Biophys. Acta* 1400, 321–339.
4. Y. Hwang, B. Wang and F. D. Bushman. 1998. Molluscum contagiosum virus topoisomerase: purification, activities and response to inhibitors. *J. Virol.* 72, 3401–3406.
5. Y. Hwang, A. Burgin and F. D. Bushman. 1999. DNA Contacts Stimulate Catalysis by a Poxvirus Topoisomerase. *J. Biol. Chem.* 274, 9160–9168.
6. A. Kornberg and T. Baker. 1991. *DNA Replication* (W. H. Freeman and Company, New York).
7. Y. Pommier, P. Pourquier, Y. Fan and D. Strumberg. 1998. Mechanism of action of eukaryotic DNA topoisomerase I and drugs targeted to the enzyme. *Biochim. Biophys. Acta* 1400, 83–106).
8. A. K. Chakraborty and H. K. Majumder. 1988. Mode of action of pentavalent antimonials: specific inhibition of type I DNA topoisomerase of *Leishmania donovani*. *Biochem. Biophys. Res. Commun.* 152, 605–611.
9. Y. Hwang, D. Rowley, D. Rhodes, J. Gertsch, W. Fenical and F. D. Bushman. 1999. Mechanism of inhibition of a poxvirus topoisomerase by the marine natural product sansalvamide A. *Mol. Pharmacol.* 55, 1049–1053.
10. J. J. Pouliot, K. C. Yao, C. A. Robertson and H. A. Nash. 1999. Yeast Gene for a Tyr-DNA Phosphodiesterase that Repairs Topoisomerase I Complexes. *Science* 286, 552–555.
11. E. Richet, P. Abcarian and H. A. Nash. 1988. Synapsis of Attachment Sites during Lambda Integrative Recombination Involves Capture of a Naked DNA by a Protein-DNA Complex. *Cell* 52, 9–17.
12. A. B. J. Burgin, B. N. Huizenga and H. A. Nash. 1995. A novel suicide substrate for DNA topoisomerases and site-specific recombinases. *Nuc. Acids Res.* 23, 2973–2979.
13. S. Shuman. 1992. DNA Strand Transfer Reactions Catalyzed by Vaccinia Topoisomerase I. *J. Biol. Chem.* 267, 8620–8627.
14. Y. Hwang, M. Park, W. H. Fischer and F. Bushman. 1999. Domain structure of the type-1B topoisomerase encoded by molluscum contagiosum virus. *Virology* 262, 479–491.
15. C. Jaxel, G. Capranico, D. Kerrigan, K. W. Kohn and Y. Pommier. 1991. Effect of Local DNA Sequence on Topoisomerase I Cleavage in the Presence or Absence of Camptothecin. *J. Biol. Chem.* 266, 20418–20423.
16. A. Tanizawa, K. W. Kohn and Y. Pommier. 1993. Induction of cleavage in topoisomerase I c-DNA by topoisomerase I enzymes from calf thymus and wheat germ in the presence and absence of camptothecin. *Nuc. Acids Res.* 21, 5157–5166.
17. Y. Fan, J. N. Weinstein, K. W. Kohn, L. M. Shi and Y. Pommier. 1998. Molecular Modeling Studies of the DNA-Topoisomerase I Ternary Cleavable Complex with Camptothecin. *J. Med. Chem.* 41, 2216–2226.
18. M. R. Redinbo, L. Stewart, P. Kuhn, J. J. Champoux and W. G. J. Hol. 1998. Crystal Structures of Human Topoisomerase I in Covalent and Noncovalent Complexes with DNA. *Science* 279, 1504–1513.
19. S. Kono, M. Ikeda, S. Tokudome and M. Kuratsune. 1988. A case-control study of gastric cancer and diet in northern Kyushu, Japan. *Jpn. J. Cancer Res.* 79, 1067–1074.
20. K. Tajima and S. Tominaga. 1985. Dietary habits and gastro-intestinal cancers: a comparative case-control study of stomach and large intestinal cancers in Nagoya, Japan. *Jpn. J. Cancer Res.* 76, 705–716.
21. S. Taniguchi, H. Fujiki, H. Kobayashi, H. Go, K. Miyado, H. Sadano and R. Shimokawa. 1992. Effect of (−)-epigallocatechin gallate, the main constituent of green tea, on lung metastasis with mouse B16 melanoma cell lines. *Cancer Letters* 65, 51–54.
22. T. Yamane, T. Takahashi, K. Kuwata, K. Oya, M. Inagake, Y. Kitao, M. Suganuma and H. Fujiki. 1995. Inhibition of N-Methyl-N'-nitro-N-nitrosoguanidine-induced Carcinogenesis by (−)-Epigallocatechin Gallate in the Rat Glandular Stomach. *Cancer Res.* 55, 2081–2084.

What is claimed is:

1. A high-throughput method of screening compounds capable of modulating topoisomerase activity comprising:
    (a) incubating at least a first nucleic acid, a topoisomerase and a potential topoisomerase-modulating compound, wherein the nucleic acid comprises at least one tag, and
    (b) assaying for a nucleic acid religation product.
2. The method of claim 1, wherein the nucleic acid is DNA.
3. The method of claim 1, wherein the nucleic acid is RNA.
4. The method of claim 1, wherein the at least one tag is a detection tag or an affinity tag.

5. The method of claim 1, wherein the method comprises incubating at least a first nucleic acid and a second nucleic acid.

6. The method of claim 5, wherein the second nucleic acid is a religation strand comprising oligonucleotides operatively associated with at least one marker tag.

7. The method of claim 6, wherein the first nucleic acid is operatively associated with an affinity tag and the second nucleic acid is operatively associated with a detection tag.

8. The method of claim 1, wherein the assay detects topoisomerase inhibitors.

9. The method of claim 1, wherein the assay detects topoisomerase activators.

10. The method of claim 1, wherein the topoisomerase is a Type I or Type III topoisomerase.

11. The method of claim 1, wherein the topoisomerase is a Type II or Type IV topoisomerase.

12. The method of claim 1, wherein assaying comprises measuring the level of nucleic acid religation activity in the presence and absence of the topoisomerase-modulating compound.

13. The method of claim 1, wherein the level of religation activity is inversely proportional to the effectiveness of the topoisomerase-modulating compound.

14. The method of claim 1, wherein step (a) is performed on a solid support.

15. The method of claim 1, wherein step (a) is performed in a liquid phase.

16. The method of claim 1, wherein the nucleic acid and topoisomerase are covalently complexed, wherein the topoisomerase retains its religation activity.

17. A method to identify a compound that modulates topoisomerase activity comprising:
   (a) incubating a reaction mixture comprising a substrate nucleic acid, a religation strand, a topoisomerase, and a candidate compound; and
   (b) assaying for ligation of the substrate nucleic acid and the religation strand.

18. A method to identify a compound that modulates topoisomerase activity comprising:
   (a) incubating a reaction mixture comprising a substrate nucleic acid, a topoisomerase, and a candidate compound; and
   (b) assaying for intramolecular ligation of the substrate nucleic acid to form a hairpin, a circular nucleic acid, or a multimer of the substrate nucleic acid.

* * * * *